US008007784B1

(12) United States Patent
Scott et al.

(10) Patent No.: US 8,007,784 B1
(45) Date of Patent: Aug. 30, 2011

(54) ANTIGENIC MODULATION OF CELLS

(75) Inventors: Mark D. Scott, Clifton Park, NY (US); John W. Eaton, Houston, TX (US)

(73) Assignee: Albany Medical College, Albany, NY (US)

( * ) Notice: Subject to any disclaimer, the term of this patent is extended or adjusted under 35 U.S.C. 154(b) by 0 days.

(21) Appl. No.: 09/323,765

(22) Filed: Jun. 1, 1999

Related U.S. Application Data

(63) Continuation-in-part of application No. 08/671,452, filed on Jun. 27, 1996, now Pat. No. 5,908,624.

(51) Int. Cl.
*A61K 35/12* (2006.01)
*A61K 35/39* (2006.01)
*C12N 5/00* (2006.01)

(52) U.S. Cl. ............... 424/93.7; 424/184.1; 435/325; 435/382; 435/177; 435/178; 435/181

(58) Field of Classification Search ............ 424/93.7, 424/93.1, 184.1; 435/325, 382, 177, 178, 435/181, 1.1
See application file for complete search history.

(56) References Cited

U.S. PATENT DOCUMENTS

| 4,179,337 A | 12/1979 | Davis et al. ............... 435/181 |
| 5,006,333 A | 4/1991 | Saifer et al. ............... 424/78 |
| 5,013,556 A | 5/1991 | Woodle et al. ............ 424/450 |
| 5,214,131 A | 5/1993 | Sano et al. ................ 530/345 |
| 5,380,536 A | 1/1995 | Hubbell et al. ............ 424/497 |
| 5,395,619 A | 3/1995 | Zalipsky et al. ........... 424/450 |
| 5,399,665 A | 3/1995 | Barrera et al. ............. 528/354 |
| 5,529,914 A | 6/1996 | Hubbell et al. ............ 435/182 |
| 5,578,442 A | 11/1996 | Desai et al. ................ 435/1.1 |
| 6,129,912 A | 10/2000 | Hortin et al. |

FOREIGN PATENT DOCUMENTS

| WO | 86/04145 | 7/1986 |
| WO | 92/05801 | 4/1992 |
| WO | 93/18649 | 9/1993 |
| WO | 95/06058 | 3/1995 |
| WO | 95/26740 | 10/1995 |
| WO | 96/21036 | 7/1996 |
| WO | 96/41606 | 12/1996 |
| WO | 97/28254 | 8/1997 |
| WO | 98/32466 | 7/1998 |

OTHER PUBLICATIONS

Lin et al., Proc. Natl. Acad. Sci. USA 71:947-951 (1974).*
Lim et al., "Microencapsulated Islets as Bioartificial Endocrine Pancreas", *Science*, 210, 908-910 (Nov. 21, 1980).
Mitz et al, "Synthesis of Biologically Active Cellulose Derivatives of Enymes", *Nature*189, A Weekly Journal of Science, 576-577, (Feb. 18, 1961).
Abuchowski, A., et al., "Alteration of Immunological Properties of Bovine Serum Albumin by Covalent Attachment of Polyethylene Glycol", *The Journal of Biological Chemistry*, 252 (11), 3578-3581, (Jun. 10, 1977).

Abuchowski, A., et al., "Effect of Covalent Attachment of Polyethylene Glycol on Immunogenicity and Circulating Life of bovine Liver Catalase", *The Journal of Biological Chemistry*, 252 (11), 3582-3586, (Jun. 10, 1977).
Chillon, M., et al., "Adenovirus complexed with polyethylene glycol and cationic lipid is shielded from neutralizing antibodies in vitro", *Gene Therapy.*, 5, 995-1002, (1998).
Fasbender, A., et al., "Complexes of adenovirus with polycationic polymers and cationic lipids increase the efficiency of gene transfer in vitro and in vivo", *The Journal of Biological Chemistry*, 272 (10), 6479-6489, (Mar. 7, 1997).
Han, D.K., et al., "Preparation and Surface Properties of PEO-Sulfonate Grafted Polyurethanes for Enhanced Blood Compatibility", *J. Biomater. Sci. Polymer Edn.*, 4 (6), 579-589, (1993).
Harris, J.M., "Laboratory Synthesis of Polyethylene Glycol Derivatives", *Macromol. Chem. Phys.*, C25 (3), 325-371, (1985).
Harris, J.M., et al., "Synthesis and Charcterization of Poly(ethylene glycol) Derivatives", *Journal of Polymer Science, Polymer Chemistry Edition.* 22,341-351, (1984).
Hunt, C.A., et al., "Synthesis and Evaluation of a Prototypal Artificial Red Cell", *Science*, 230, 1165-1168, (Dec. 6, 1985).
Jackson, C.C., et al., "Synthesis, Isolation, and Characterization of Conjugates of Ovalbumin with Monomethoxypolyethylene Glycol Using Cyanuric Chloride as the Coupling Agent", *Analytical Biochemistry*, 165, 114-127, (1987).
Jeong, S.T., et al., "Decreased Agglutinability of Methoxy-Polyethylene Glycol Attached Red Blood Cells: Significance as a Blood Substitute", *Art. Cells, Blood Subs., and Immob. Biotech*, 24 (5), 503-511, (1996).
Klibanov, A.L., et al., "Activity of amphipathic poly(ethylene glycol) 5000 to prolong the circulation time of liposomes depends on the liposome size and is unfaavorabale for immunoliposome binding to target", *Biochimica et Biophysica Acta*, 1062, 142-148, (1991).
Lacy, P.E., et al., "Maintenance of Normoglycemia in Diabetic Mice by Subcutaneous Xemografts of Encapsulated Islets", *Science*, 254, 1782-1784, (Sep. 27, 1991).
Lasic, D., "Liposomes-Synthetic lipid microspheres serve as multipurpose vehicles for the delivery of drugs, genetic material and cosmetics", *American Scientist*, 80, 20-31 (Jan.-Feb. 1992).

(Continued)

*Primary Examiner* — Robert C Hayes
(74) *Attorney, Agent, or Firm* — Mark A. Litman & Associates, P.A.

(57) ABSTRACT

The present invention is directed to a non-immunogenic cellular composition comprising: a cell having a cell surface and antigenic determinants on the cell surface; an optional linker molecule covalently attached to the cell surface; and a hydrophilic, biocompatible, non-immunogenicity providing compound or polymer (e.g., polyethylene glycol or a derivative thereof) covalently attached to the linker molecule or directly to the cell. In one embodiment, the linker molecule is covalently attached directly to the antigenic determinant on the cell surface. In an alternate embodiment, the linker molecule may be covalently attached to a non-antigenic site on the cell surface, but will camouflage the antigenic determinant on the cell surface. Various uses of the resulting non-immunogenic cell are also provided, including a method of decreasing phagocytosis of a cell, a method of decreasing an adverse reaction to a transfusion, a method of decreasing rejection of a transplanted cell, tissue or organ, and a method of decreasing antibody-induced aggregation of cells.

12 Claims, 13 Drawing Sheets

OTHER PUBLICATIONS

Maruyama, K., et al., "Prolonged circulation time in vivo of large unilamellar liposomes composed of distearoyl phosphatidycholine and cholesterol containing amphipathic poly(ethylene glycol)", *Biochimica et Biophysica Acta*, 1128, 44-49, (1992).

Merrill, E.W., *Poly(Ethylene Glycol) Chemistry: Biotechnical and Biomedical Applications*, Chapter 14: Poly (Ethylene Oxide) and Blood Contact—A Chronicle of One Laboratory, 199-200, (1992).

Park, K.D., et al., *Poly(Ethylene Glycol) Chemistry: Biotechnical and Biomedical Applications*, Chapter 18: PEO-Modified Surfaces—In Vivo, Ex Vivo, and In Vivo Blood Compatibility, 283-301, (1992).

Sawhney, A.S., et al., "Modification of Islet of Langerhans surfaces with Immunoprotective Poly(ethylene glycol) Coatings via Interfacial Photopolymerization", *Biotechnology and Bioengineering*, 44, 383-386, (1994).

Senior, J., et al., "Influence of surface hydrophilicity of liposomes on their interaction with plasma protein and clearance from the circulation: studies with poly(ethylene glycol) -coated vesicles", *Biochimica et Biophysica Acta*, 1062, 77-82, (1991).

Vichinsky, E.P., et al., "Alloimmunization in Sickle Cell Anemia and Transfusion of Racially Unmatched Blood", *The New England Journal of Medicine*, 322 (23), 1617-1621, (Jun. 7, 1990).

Von Specht, B.U., et al., "Polyvinylpyrrolidone as a Soluble Carrier of Proteins", *Hoppe-Seyler's Zeitschrift Fur Physiologische Chemie*, 354 (12), 1659-1660, (Dec. 1973).

Zalipsky, S., et al., *Poly(Ethylene Glycol) Chemistry: Biotechnical and Biomedical Applications*, Chapter 21: Use of Functionalized Poly (Ethylene Glycol)s for Modification of Polypeptides, 346-370, (1992).

* cited by examiner

= Activated PEG
= Antigenic Site
= Antigenic Site

FIG. 2

ANTIGENIC MODULATION OF CELLS

CROSS-REFERENCE TO RELATED APPLICATION

This application is a continuation-in-part of Ser. No. 08/671,452 filed Jun. 27, 1996 now U.S. Pat. No. 5,908,624.

The subject matter of this application was made with support from the United States Government under grant RO1 HL53066 of the National Institutes of Health. The Government has certain rights in the invention.

BACKGROUND OF THE INVENTION

1. Field of the Invention

The present invention relates generally to antigenic modulation of cells, and more particularly to non-immunogenic cellular compositions comprising cells modified with a hydrophilic, biocompatible, non-immunogenicity providing compound or polymer, and uses of such non-immunogenic cells.

2. Background of the Art

Throughout this application various publications are referenced, many in parenthesis. Full citations for these publications are provided at the end of the Detailed Description. The disclosures of these publications in their entireties are hereby incorporated by reference in this application.

Acute tissue rejection can be observed in two major clinical situations: 1) blood transfusions; and 2) organ transplantation. In both situations, to be described in greater detail below, antibody binding and complement fixation are the two major mechanisms underlying the destruction of the donor tissue (the donor tissue referring to blood or organs). Previous means of attempting to control acute rejection have centered on tissue matching and pharmacologic interventions. Despite these measures a significant number of often life-threatening acute tissue rejection reactions continue to occur.

Blood transfusions are a crucial component in the treatment of a number of acute and chronic medical problems. These range from massive blood loss following traumatic injury to chronic transfusions to treat diseases such as thalassemia and sickle cell anemia. In most acute injuries simple blood typing (ABO/rh) is sufficient to identify appropriate donors. Occasionally, however, rare blood types are encountered where an appropriate match cannot be quickly found, a situation which may be life-threatening. More often problems are encountered in individuals, usually minorities, receiving chronic transfusions (e.g., as in sickle cell anemia and the thalassemias). Often, simple blood typing becomes insufficient in determining a proper match because these individuals develop transfusion reactions to minor red blood cell antigens. The transfusion reactions to these minor red blood cell antigens can make it nearly impossible to identify appropriate blood donors (Vichinsky et al. 1990).

To date, the only solutions to the above situations are to store autologous blood (frozen or at 4° C.), keep a blood bank registry of potential donors with rare blood types, and to encourage minority blood donations. While all of these steps are prudent and variably effective, situations still arise where an appropriate (or even satisfactory) blood match cannot be made. Therefore, a need exists for methods and agents which will disguise otherwise immunogenic (or directly immunologically recognizable) red blood cells.

Similarly, the transplantation of organs (such as kidneys and livers) from one human to another is often made difficult by a lack of exact immunologic identify between donor and recipient. Sometimes, the transplanted organ is subject to direct attack by the immune system of the recipient even before a secondary immunologic response has had time to occur. This so-called 'hyperacute rejection' is often life threatening and, obviously, prevents the effective integration of the transplant into the recipient. Therefore, a need exists for methods and agents which may prevent immediate recognition of the endothelial surfaces of organ transplants, thereby moderating or stopping the process of acute graft rejection. In a similar vein, the transplantation of organs from one species to another ("xenotransplantation") faces even more formidable immunologic barriers and would be greatly facilitated by methods for blocking immunologic recognition of the foreign endothelial surface.

Proteins have been modified by the covalent attachment of soluble polymers such as polyvinyl alcohol, carboxymethyl cellulose (Mitz and Summaria 1961), and polyvinylpyrrolidone (von Spect et al. 1973). Various purified antigenic proteins have also been modified by covalent attachment of polyethylene glycols (PEGs) to render the resulting proteins non-immunogenic. Abuchowski et al. (1977a) disclose the modification of purified bovine serum albumin (BSA) by covalent attachment of methoxypolyethylene glycol, rendering the BSA non-immunogenic. Abuchowski et al. (1977b) disclose the modification of purified bovine liver catalase by covalent attachment of methoxypolyethylene glycol, rendering the catalase non-immunogenic. Jackson et al. (1987) disclose the modification of purified ovalbumin with monomethoxypolyethylene glycol using cyanuric chloride as a coupling agent. The resulting ovalbumin is non-immunogenic. Various reports have also shown that polyethylene glycol (PEG) coated liposomes have improved circulation time (Klivanov et al. 1991; Senior et al. 1991; Maruyama et al. 1992; and Lasic 1992).

Islets of Langerhans have been microencapsulated in semipermeable membranes in order to decrease immunogenicity of implanted islets (Lacy et al. 1991; Lim 1980). Sawhney et al. (1994) coated rat islets with a polyethylene glycol tetraarylate hydrogel. Importantly, PEG was not directly incorporated into the islet cell membranes but rather the cells were surrounded by the PEG-containing hydrogel.

Zalipsky and Lee (1992) discuss the use of functionalized polyethylene glycols for modification of polypeptides, while Merrill (1992) and Park and Wan Kim (1992) both disclose protein modification with polyethylene oxide.

U.S. Pat. No. 4,179,337 of Davis et al. discloses purified polypeptides, such as enzymes and insulin, which are coupled to polyethylene glycol or polypropylene glycol having a molecular weight of 500 to 20,000 daltons to provide a physiologically active non-immunogenic water soluble polypeptide composition. The polyethylene glycol or polypropylene glycol protect the polypeptide from loss of activity and the composition can be injected into the mammalian circulatory system with substantially no immunogenic response.

U.S. Pat. No. 5,006,333 of Saifer et al. discloses a biologically persistent, water-soluble, substantially non-immunogenic, substantially non-antigenic conjugate of superoxide dismutase, prepared by coupling purified superoxide dismutase to one to five strands of a polyalkylene glycol which is polyethylene glycol or polyethylene-polypropylene glycol copolymer, wherein the polyalkylene glycol has an average molecular weight of about 35,000-1,000,000.

U.S. Pat. No. 5,013,556 of Woodle et al. discloses a liposome composition which contains between 1-20 mole percent of an amphipathic lipid derivatized with a polyalkylether, as exemplified by phosphatidylethanolamine derivatized with polyethylene glycol.

U.S. Pat. No. 5,214,131 of Sano et al. discloses a polyethylene glycol derivative, a purified peptide modified by the polyethylene glycol derivative, and a method for production thereof. The polyethylene glycol derivative is capable of modifying the guanidine groups in peptides. The peptides modified by the polyethylene glycol derivative are extremely stable, are considerably delayed in biological clearance, and retain their physiological activities over a long period.

WO 95/06058 (hereinafter referred to as Francis) describes a process for the modification of polymers, particularly for producing adducts of polymers and a target material. Example 13 shows the reaction of biactivated tresylPEG (polyethyleneglycol) with erythropoietin and Example 7 shows the reaction of human erythrocytes with tresylated methylPEG.

A need continues to exist for methods of making entire cells and tissues and organs, as opposed to purified proteins or peptides, non-immunogenic.

SUMMARY OF THE INVENTION

The invention provides a method for modulating the antigenicity and aggregation of mammalian, preferably human, cells. To this end, the subject invention provides for the covalent binding of a hydrophilic, biocompatible, non-immunogenicity providing compound or polymer to intact cells. Cells that can be effectively modified in accord with the invention include anucleate or anuclear cells (platelets and red blood cells) and nucleated cells (epithelial cells, endothelial cells, and lymphocytes). In one embodiment, the hydrophilic, biocompatible, non-immunogenicity providing compound or polymer compound is polyethylene glycol (PEG) or a derivative thereof. Potential applications for PEG modification of cells include: 1) PEG-derivatized red blood cells (RBC) to diminish transfusion reactions arising from mismatched blood or sensitization to minor blood group antigens due to chronic transfusions; 2) PEG-derivatization of the vascular endothelium of donor tissues prior to transplantation to prevent/diminish acute tissue rejection; 3) implantation of PEG-derivatized cells to correct enzyme deficiencies, other inborn errors of metabolism, or other types of defective cellular functions, and 4) transfusion of derivatized RBC into malaria-infected individuals to correct the accompanying acute anemia and prevent the infection of the transfused cells. Unexpectedly, red blood cells modified by PEG have normal in vitro and in vivo survival when compared to control cells. The cells may retain their biological effectiveness after conversion to non-immunogenic cells by attachment of the hydrophilic, biocompatible, non-immunogenicity providing compound or polymer.

Covalent linkage of hydrophilic, biocompatible, non-immunogenicity providing compounds or polymers (e.g., PEG or PEG-derivatives, such a methoxypolyethylene glycol or PEG-like compounds such as polyethylene oxide, and particularly non-ionic hydrophilic, biocompatible, non-immunogenicity providing compounds or polymers. The term non-ionic generally means that the compound or group does not have a high dissociation constant so that the majority of the compounds or groups will not provide a definitive electrical charge.), directly or indirectly to membrane proteins of cells decreases the antigenic recognition of these cells. Some of the available reactions and reagents to accomplish this are summarized in FIG. 1. Similarly, insertion of PEG-modified phospholipids/free fatty acids into the cell membrane may serve a similar purpose. The examples hereinbelow demonstrate that unexpectedly (1) it is possible to derivatize normal red blood cells and other cells with PEG without causing lysis, (2) that the derivatized red blood cells remain intact and exhibit normal morphology, (3) that PEG modification of the cell surface does, indeed, 'hide' antigenic determinants such as ABO blood groups, epithelial cell-specific antigens (ESA) and the MHC antigens which underlie tissue/organ rejection, (4) that the derivatized cells survive normally in the circulation of experimental animals, and (5) that PEG derivatized red blood cells from one species have vastly improved survival in the circulation of an animal from another species.

As delineated above, transfusion reactions (to both major and minor red blood cell antigens) represent a significant clinical problem. In most cases, these transfusion reactions actually result from minor surface antigens not routinely measured by blood banks. In situations where either an appropriate blood type match cannot be located or, more often, when sensitization to minor red blood cell antigens has occurred, PEG-modified red blood cells can be employed to diminish/prevent the recognition of red blood cell antigenic determinants. The application of this invention can also lead to procedures for modification of animal red blood cells which can then be used for transfusion into humans, or into animals of the same or other species. The application of this invention can further lead to procedures for modification of red blood cells to prevent malarial invasion or opsonization by factors such as complement.

In addition, based on the data contained in this disclosure, the scope of this invention extends well beyond blood banking to other areas where foreign tissues are manipulated or introduced in vitro or in vivo. One area of primary interest is the use of PEG-modified tissues (especially covalent modification of the vascular endothelium) for tissue transplantation. Despite appropriate HLA-matches, many organ transplants fail as a result of immediate tissue rejection. This rejection reaction occurs primarily at the level of the vascular endothelium and results in vessel occlusion, tissue hypoxia/ischemia and ultimate loss of the organ transplant. Based on the chemistry of PEG-cell derivatization disclosed herein, it is possible to perfuse the vasculature of the tissue with a solution of activated PEG. This will modify the vessel walls (i.e., endothelial cells) which will prevent or diminish the aforementioned immediate tissue rejection. This technology can thus improve the rate of successful tissue engraftment.

The invention thus provides a non-immunogenic cellular composition comprising: a cell having a cell surface and antigenic determinants on the cell surface; and a hydrophilic, biocompatible, non-immunogenicity providing compound or polymer covalently attached to the cell surface directly or by means of the linking moiety, which linking moiety can be derived from a linker molecule, as discussed below. The hydrophilic, biocompatible, non-immunogenicity providing compound or polymer acts to block recognition of the antigenic determinants on the cell surface. In one embodiment, the linking moiety is covalently attached directly to the antigenic determinant on the cell surface. In an alternate embodiment, the linking moiety may be covalently attached to a non-antigenic site of the cell surface, the antigenic site on the cell surface is camouflaged or masked by virtue of the long chain length of the hydrophilic, biocompatible, non-immunogenicity providing compound or polymer.

The invention further provides a method of producing a non-immunogenic cell. The method comprises: covalently attaching a hydrophilic, biocompatible, non-immunogenicity providing compound or polymer to the surface of the cell directly, or by means of a linking moiety, so that hydrophilic, biocompatible, non-immunogenicity providing compound or polymer blocks recognition of antigenic determinants on the cell surface to produce a non-immunogenic cell. A non-immunogenic cell produced by this method is also provided by the subject invention.

The concept of the subject invention can also provide a method of decreasing phagocytosis of a cell. This method comprises: selecting a cell for introduction into a subject, the cell having a cell surface and antigenic determinants on the cell surface; covalently attaching an amount of a hydrophilic, biocompatible, non-immunogenicity providing compound or polymer to the cell surface directly or by means of a linking moiety, so that the attached hydrophilic, biocompatible, non-immunogenicity providing compound or polymer blocks recognition of antigenic determinants on the cell surface to produce a non-immunogenic cell; and introducing the non-immunogenic cells into a subject, wherein phagocytosis of the non-immunogenic cell is decreased as compared to phagocytosis of the cell prior to modification.

Further provided is a method of decreasing an adverse reaction to a transfusion, the method comprising: selecting a red blood cell for transfusion into a subject, the red blood cell having cell surface and blood group antigenic determinants on the cell surface; covalently attaching a hydrophilic, biocompatible, non-immunogenicity providing compound or polymer capable of blocking the blood group antigenic determinants on the cell surface, to the cell surface directly or by means of a linking moiety, so as to produce a non-immunogenic red blood cell; and transfusing a subject with the non-immunogenic red blood cell, wherein adverse reaction to the transfusion of the non-immunogenic red blood cell is decreased as compared to transfusion of the red blood cell prior to modification.

Also provided is a method of decreasing rejection of a transplanted cell, the method comprising: selecting a cell for transplantation into a subject, the cell having a cell surface and antigenic determinants on the cell surface; covalently attaching a hydrophilic, biocompatible, non-immunogenicity providing compound or polymer capable of blocking the recognition of the antigenic determinants on the cell surface, to the cell surface directly or by means of a linking moiety, so as to produce a non-immunogenic cell; and transplanting the non-immunogenic cell into a subject, wherein rejection of the transplanted cell is decreased as compared to rejection of the cell prior to modification.

The invention provides a method of decreasing aggregation of nucleated and anucleate cells such as that induced by antibodies or by other cell:cell interactions. The method comprises: covalently attaching hydrophilic, biocompatible, non-immunogenicity providing compounds or polymers capable of blocking recognition of antigenic determinants on a cell surface to the cell surface of each of a plurality of cells directly or by means of a linking moiety, so as to produce non-aggregating cells, wherein antibody-induced aggregation of the non-aggregating cells is decreased as compared to antibody-induced aggregation of the cells prior to modification.

As used herein, the term "linking moiety" or "linker" refers to an at least divalent organic group that covalently, or by complexation or chelation binds to both the hydrophilic, biocompatible, non-immunogenicity providing compound or polymer molecule and the cell surface, to attach at least one non-immunogenic compound to at least one functional group or structure on the cell surface. The linking moieties can be derived from reactive linker molecules, as described hereinbelow.

BRIEF DESCRIPTION OF THE FIGURES

These and other features and advantages of this invention will be evident from the following description of preferred embodiment when read in conjunction with the accompanying drawings in which:

FIG. 2 is a schematic depiction of a further embodiment of a non-immunogenic cellular composition according to the subject invention. In this embodiment, the hydrophilic, biocompatible, non-immunogenicity providing compound or polymer is polyethylene glycol or a derivative thereof and the activated PEG (PEG-linker) is covalently attached to antigenic determinants on the cell surface (directly blocking antigenic sites) and also covalently attached to non-antigenic sites on the cell surface (indirectly blocking antigenic sites due to their long chain length);

DETAILED DESCRIPTION OF THE INVENTION

Figure 1:
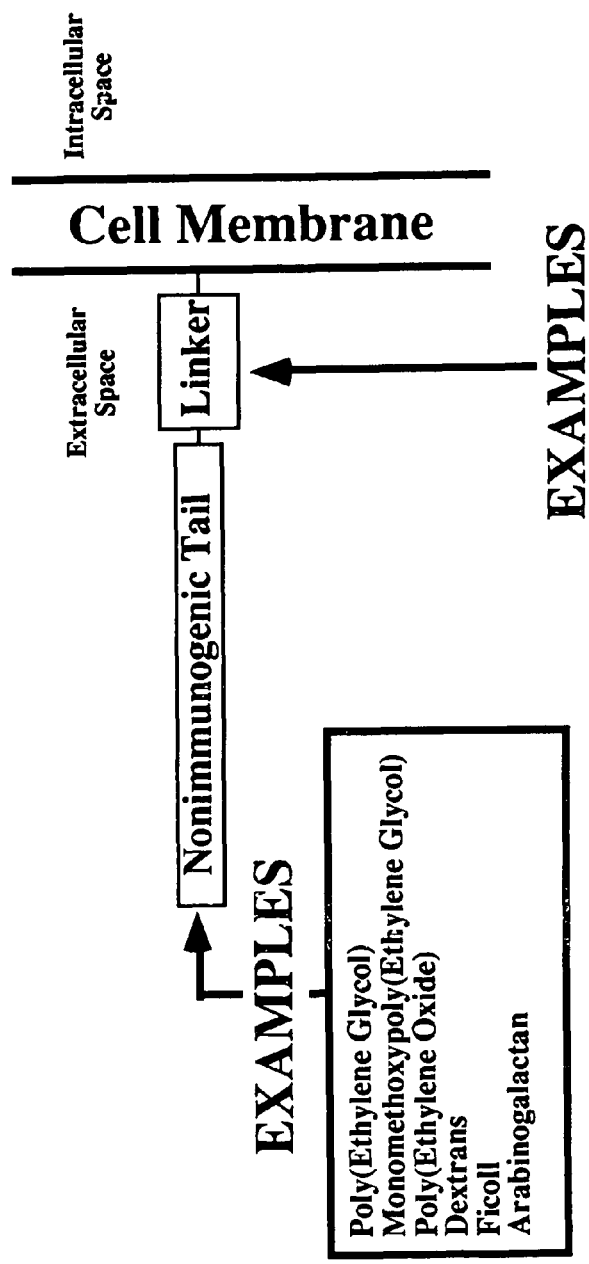
FIG. 1 is a schematic depiction of the preparation of certain embodiments of the non-immunogenic cellular compositions according to the subject invention.
Figure 1:
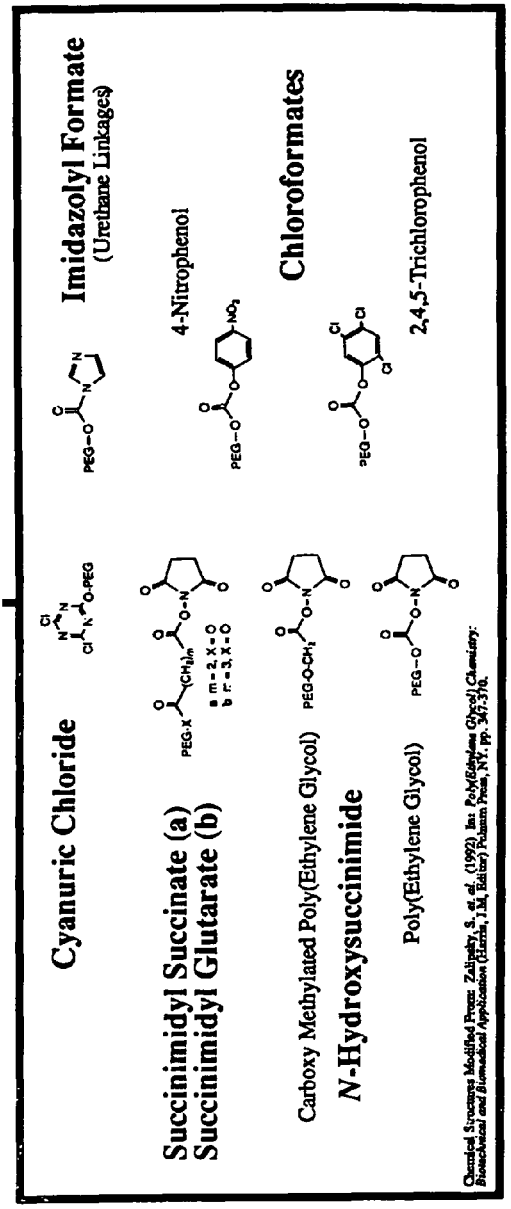

The present invention provides a non-immunogenic cellular composition comprising: a cell having a cell surface and antigenic determinants on the cell surface; a linking moiety covalently attached to the cell surface; and at least one hydrophilic, biocompatible, non-immunogenicity providing compound or polymer covalently attached to the linking moiety and capable of blocking recognition of the antigenic determinants on the cell surface. Alternatively, the at least one hydrophilic, biocompatible, non-immunogenicity providing compound or polymer can be bound directly to the cell surface, if it comprises groups such as carboxylic acids, aldehydes, ketals or acetals that are reactive with $NH_2$ or SH groups on the cell surface.

The invention may be alternatively described as:

A non-aggregating, non-immunogenic anuclear cellular composition comprising:
   a) a mammalian anuclear cell having a cell surface and antigenic determinants on said surface;
   b) a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer;

A non-immunogenic nuclear cellular composition in which at least 25% by number of nuclear cells in said composition remain viable for 96 hours comprising:
   a) a mammalian nuclear cell having a cell surface and antigenic determinants on said surface;
   b) a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer;

A non-immunogenic nuclear cellular composition having insufficient amounts of toxic materials within said composition to be toxic to nuclear cells within said composition comprising:
   a) a mammalian nuclear cell having a cell surface and antigenic determinants on said surface;
   b) a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer;

A non-immunogenic anuclear or nuclear cellular composition comprising:
   a) a mammalian anuclear or nuclear cell having a cell surface and antigenic determinants on said surface;
   b) a sufficient amount of hydrophilic, biocompatible, non-immunogenicity providing compound or polymer covalently attached to said anuclear or nuclear surface so that recognition of said antigenic determinants on said anuclear or nuclear cell surface is blocked by said covalently bonded hydrophilic, biocompatible, non-immunogenicity providing compound or polymer. Said composition being free of any by-products from the covalent attachment of said hydrophilic, biocompatible, non-immunogenicity providing compound or polymer to said anuclear or nuclear cell surface;

A non-immunogenic cellular composition having insufficient amounts of toxic materials within said composition to be toxic to said cells comprising:
   a) a mammalian cell having a cell surface and antigenic determinants on said surface;
   b) a sufficient amount of covalently attached to said anuclear or nuclear surface so that recognition of said antigenic determinants on said anuclear or nuclear cell surface is blocked by said covalently bonded hydrophilic, biocompatible, non-immunogenicity providing compound or polymer; or A viable non-immunogenic nuclear cellular composition comprising:
   a) a mammalian nuclear cell having a cell surface and antigenic determinants on said surface;
   b) a sufficient amount of covalently attached to said cell surface so that recognition of said antigenic determinants on said cell surface is blocked by said covalently bonded hydrophilic, biocompatible, non-immunogenicity providing compound or polymer.

The cell can be any suitable cell with accessible antigenic determinants on the cell's surface. Suitable cells include anuclear cells, for example, hematopoietic cells, i.e., red blood cells or platelets, or nucleated cells, for example, vascular endothelial cells, PBMCs, hepatic cells, neuronal cells, pancreatic cells, or epithelial cells.

The antigenic determinants on the cell surface can be due to the presence of antigenic proteins, antigenic carbohydrates, antigenic sugars, antigenic lipids, antigenic glycolipids, antigenic glycoproteins, etc. "Antigenic" determinants can also be involved in malarial invasion of a cell, or opsonization of a cell. For example, red blood cells have antigens on their surface which determine ABO/rh blood types. These antigens are often referred to as blood group antigenic determinants. These antigens are recognized by an incompatible host and the donor cell will be rapidly destroyed. This can involve the enhancement of natural immunity (through phagocytes, such as macrophages, neutrophils, and natural killer cells) or the stimulation of specific or acquired immunity (including humoral immunity through antibodies and cell-mediated immunity through T lymphocytes). In any event, the cell is recognized as foreign and elicits an immune response.

In order to prevent this immune response from destroying the cell, the subject invention involves modification of the antigenicity of the cell. This modification is accomplished by attaching a hydrophilic, biocompatible, non-immunogenicity providing compound or polymer to the cell. Suitable hydrophilic, biocompatible, non-immunogenicity providing compound or polymer for use in the subject invention include non-immunogenic compounds capable of blocking recognition of antigenic determinants on the cell surface. The compounds are generally long chain hydrophilic, biocompatible compounds, wherein the long chain can sterically block the antigenic determinants. Such hydrophilic, biocompatible, non-immunogenicity providing compound or polymer include polyalkylene glycols such as polyethylene glycol, polypropylene glycol, mixed polypropylene-polyethylene glycols, or derivatives thereof (including monomethoxypolyethylene glycol), certain polysaccharides such as dextrans, cellulosics, Ficoll, and arabinogalactan, as well as synthetic polymers such as polyurethanes. Useful molecular weights of these compounds can range from about 100-500 to 100,000-200,000 Daltons or above.

Figure 2:
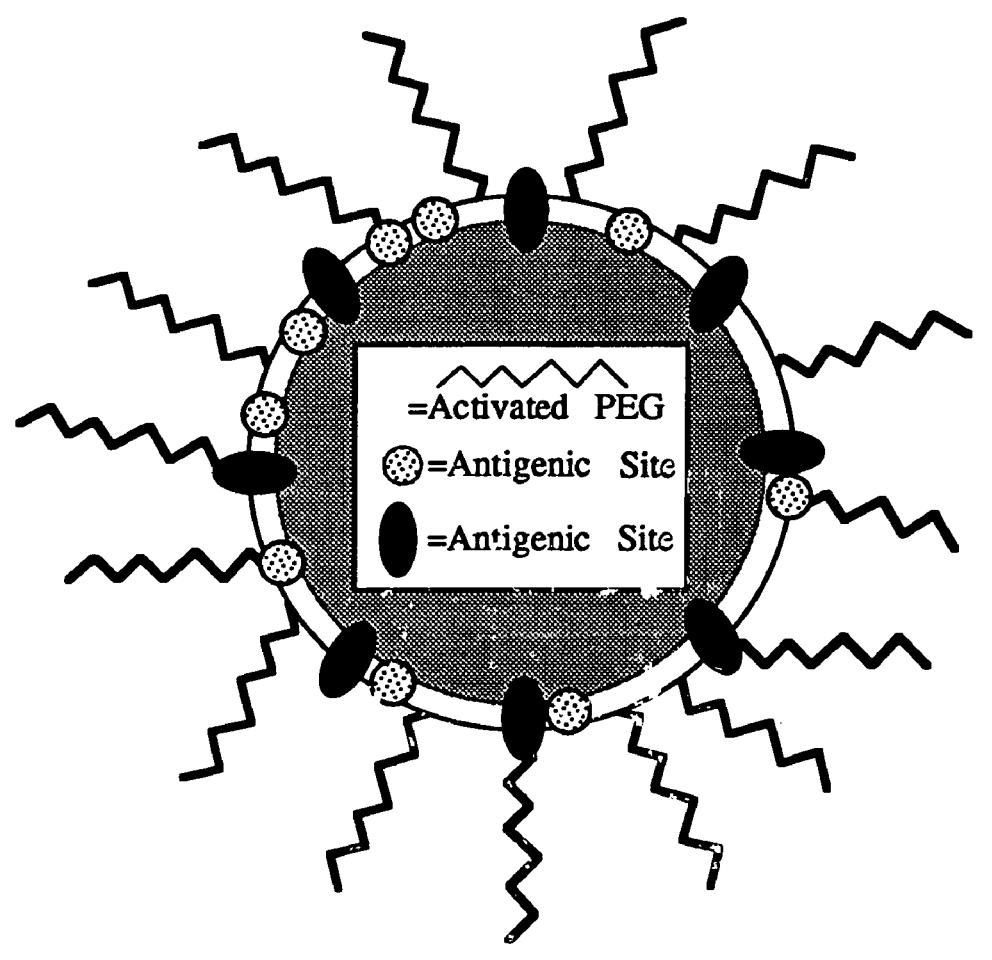

The presently preferred hydrophilic, biocompatible, non-immunogenicity providing compound or polymer according to the subject invention is polyethylene glycol or a derivative thereof. The polyethylene glycol or derivative thereof is a molecule with a very long chain length. The hydrophilic, biocompatible, non-immunogenicity providing compound or polymer (e.g., polyethylene glycol or derivative thereof) can be directly attached to an antigenic site (e.g., an antigenic determinant) on a cell surface via a linking moiety (direct modification of antigenicity) (see FIG. 1 and FIG. 2) or can be attached to a non-antigenic site on the cell surface via a linking moiety. In both cases, the long chain of the hydrophilic, biocompatible, non-immunogenicity providing compound or polymer (e.g., polyethylene glycol or derivative thereof) effectively blocks antigenic sites on the cell surface (indirect modification of antigenicity) (see FIG. 2). In either embodiment, the hydrophilic, biocompatible, non-immunogenicity providing compound or polymer (e.g., polyethylene glycol or derivative thereof) is attached to the cell surface by a linking moiety, which is derived from a linker molecule that can react with the PEG. The combination of a polyethylene glycol or derivative thereof and the linker molecule is generally referred to as an "activated" polyethylene glycol or derivative thereof.

Polyethylene glycols (PEG) and derivatives thereof are well known hydrophilic compounds and moieties in the art. Polyethylene glycol has the formula $$H(OCH_2CH_2)_nOH$$

wherein n is greater than or equal to 4, with a molecular weight of up to about 20,000 Daltons. However, PEGs and derivatives thereof are available having molecular weights of 200,000 Daltons and above, and can be used in the practice of the present invention, alone, or in combination with lower m.w. materials.

Various derivatives of polyethylene glycol comprise substitutes for the H or OH end groups, forming, for example, polyethylene glycol ethers (such as PEG-O—R; PEG-O—$CH_3$; $CH_3$-PEG-OH or "mPEG"; 2,4-dinitrophenyl ethers of PEG), polyethylene glycol esters (such as PEG-$O_2C(CH_2)_{14}$$CH_3$; PEG-$O_2CCH_2CH_2CO_2$-atropine), polyethylene glycol amides (such as PEG-$O_2C(CH_2)_7CONHR$; mPEG-$O_2CCH_2CH_2CONH(CH_3)CHCH_2C_6H_5$; PEG-$O_2CCH_2CH_2CONHCH_2CH_2$—$NAD^+$), polyethylene glycol amines (such as PEG-$NH_2$; PEG-$NH(CH_2)_6NH_2$; PEG-$OCH_2CH_2NH_2$; mPEG-$NH_2$), polyethylene glycol acids (such as PEG-$O_2C(CH_2)_2CO_2H$; PEG-$OCH_2CO_2H$; PEG-$O_2C(CH_2)_7$—$CO_2H$), polyethylene glycol aldehydes (PEG-O—$CH_2$—CHO), and electrophilic derivatives (such as PEG-Br; PET-$OSO_2CH_3$; PEG-OTs). Various phenyl moieties can also be substituted for the H or OH of PEG, such as the 2,4-dinitrophenyl ether of PEG mentioned above).

For a full discussion of polyethylene glycol and activated derivatives thereof, including the synthesis of the derivatives, see the following references: Harris et al. 1984; Harris 1985; Zalipsky and Lee 1992; Park and Kim 1992; Merrill 1992; and U.S. Pat. Nos. 4,179,337 and 5,214,131, the contents of each of which are incorporated herein by reference. The particular non-immunogenic compounds, including the polyethylene glycol derivatives, listed above are exemplary only, and the invention is not intended to be limited to those particular examples.

According to the subject invention, these hydrophilic, biocompatible, non-immunogenicity providing compound or polymer (e.g., polyethylene glycol molecules or derivatives thereof) are covalently attached to the cell surface by means of a linking moiety. The hydrophilic, biocompatible, non-immunogenicity providing compound or polymer are not merely ionically attached, which would allow the groups to be too easily removed and environmentally dependent for stability. These linking moieties can be prepared by reaction of the polyethylene glycol or derivative thereof with suitable linker molecules that are also well known in the art, and include, for example, cyanuric chloride, imidazolyl formate, succinimidyl succinate, succinimidyl glutarate, N-hydroxysuccinimide, 4-nitrophenol, and 2,4,5-trichlorophenol. These linker molecules 'activate" the PEG, a term also well known in the art. For a description of activation of PEG, with examples of known linking moieties and molecules, see Harris 1985. The linker molecules listed above are exemplary only, and the invention is not intended to be limited to those particular examples. As would be recognized by one of skill in the art, the linking molecules disclosed hereinabove and on FIG. 1 react with a reactive group such as a hydroxy of the hydrophilic, biocompatible, non-immunogenicity providing compound or polymer, e.g., the PEG or MPEG, and also react with an $NH_2$ or, in some cases, SH, group of a peptidyl or other amino acid residue on the cell surface to covalently join them, whereby the linking molecule is converted in one or more steps into a divalent linking moiety such as shown on Table 1, below.

TABLE 1

Linking Moiety

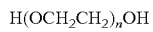

| [Non-immunogenic compound]-O— | ![triazine with Cl] | —NH-Cell |
| --- | --- | --- |
| | —$CH_2$— | |
| —$CH_2$—CH(OH)—$CH_2$—O—⟨phenyl⟩—N=N— | | |
| —C(O)— or —C(S)— | —$(CH_2)_{2-3}$— | |
| —C(O)—$(CH_2)_{2-3}$—C(O)— | —C(O) | |
| —⟨phenyl⟩—N=N— —$CH_2$—C(O)— | | |

A number of "activated" methoxypolyethylene glycols are commercially available, in which mPEG (m.w. 5000) has been bound to a linking molecule at the hydroxyl terminus. These include, methoxypolyethylene glycol (mPEG) para-nitrophenyl carbonate, mPEG cyanuric chloride, mPEG-succinimidyl succinate, mPEG tresylate, and mPEG imidazolyl carbonyl. For example, see I. Jackson et al., *Anal Biochem.*, 565, 114 (1987); A. Abuchowski et al., *J. Biol. Chem.*, 252, 3578 (1977); F. M. Veronese et al., *Appl. Biochem. Biotech.*, 11, 141 (1985), C. Delgado et al., *Biotech. Appl. Biochem.*, 12, 119 (1990); C. O. Veavchemp et al., *Anal. Biochem*, 131, 25 (1983).

The chemistry involved in the covalent attachment of the hydrophilic, biocompatible, non-immunogenicity providing compound or polymer (such as PEG or a derivative thereof) to reactive groups such as proteins and peptides on the cell surface (thus, covalent attachment of the hydrophilic, biocompatible, non-immunogenicity providing compound or polymer to a cell surface) by means of linking moieties, is known in the art, and is discussed in detail in Harris 1985; Harris et al. 1984; and Zalipsky and Lee 1992. Because polyethylene glycol and its derivatives are very well known in the art, including the synthesis and modification thereof, including attachment to proteins, further details are not disclosed herein relating to this aspect of the invention, other than the examples that follow.

Having thus identified the non-immunogenic cellular composition according to the subject invention, various uses of the invention are possible.

The invention thus further provides a method of producing a non-immunogenic cell. The method comprises: covalently attaching a hydrophilic, biocompatible, non-immunogenicity providing compound or polymer capable of blocking recognition of antigenic determinants on a cell surface, to a cell surface, directly, or by means of a linking moiety, so as to produce a non-immunogenic cell. If the cell is a red blood cell, the method can further comprise transfusing a subject with the non-immunogenic cell. Since the antigenic determinants, such as the blood group antigenic determinants, on the red blood cell are blocked by the hydrophilic, biocompatible, non-immunogenicity providing compound or polymer, the transfused non-immunogenic red blood cell will not elicit an immune response. As discussed above, this method can be very useful when red blood cells need to be transfused quickly without the availability of complete blood typing or cross-matching, or when unmatched from a subject is available.

If the cell is part of a tissue or organ, the method can further comprise transplanting the non-immunogenic tissue or organ into a subject. Since the antigenic determinants on the tissue or organ, such as the vascular endothelial cells which form an exposed antigenic surface of the tissue or organ, are blocked by the hydrophilic, biocompatible, non-immunogenicity providing compound or polymer, the transplanted non-immunogenic tissue or organ will not elicit an immune response. As discussed above, this method is very useful to avoid severe rejection reactions, or graft vs. host disease, when organs or tissues are transplanted.

The invention further provides a non-immunogenic cell produced by the above method.

The concept of the subject invention can also provide a method of decreasing phagocytosis of a cell. This method comprises: introducing the non-immunogenic cell into a subject, wherein phagocytosis of the non-immunogenic cell is decreased as compared to phagocytosis of the cell prior to modification. The non-immunogenic cell can be prepared by a process comprising: selecting a cell for introduction into a subject, the cell having a cell surface and antigenic determinants on the cell surface; covalently attaching to the cell surface, directly or by means of a linking moiety, a hydrophilic, biocompatible, non-immunogenicity providing compound or polymer that blocks recognition of the antigenic determinants on the cell surface, so as to produce a non-immunogenic cell. In the case where the cell is a red blood cell, this method can prevent phagocytosis of the "foreign" red blood cell, by rendering the red blood cell non-immunogenic. The "foreign" red blood cell may be from another human, or may be from another non-human subject. In either case, the body's response would be to attempt to eliminate the "foreign" red blood cell including by phagocytosis.

Further provided is a method of decreasing an adverse reaction to a transfusion, the method comprising: transfusing a subject with the non-immunogenic red blood cell, wherein adverse reaction to the transfusion of the non-immunogenic red blood cell is decreased as compared to transfusion of the red blood cell prior to modification. The non-immunogenic red blood cells are prepared by selecting a red blood cell for transfusion into a subject, the red blood cell having a cell surface and blood group antigenic determinants on the cell surface; covalently attaching to the cell surface a hydrophilic, biocompatible, non-immunogenicity providing compound or polymer in an amount capable of blocking the blood group antigenic determinants on the cell surface; wherein the compound is covalently attached to the cell surface directly or by means of a linking moiety, so as to produce a non-immunogenic red blood cell. As discussed above, the red blood cell could be from another human or from a non-human mammal.

Also provided is a method of deceasing rejection of a transplanted cell, the method comprising: transplanting a non-immunogenic modified cell into a subject, wherein rejection of the transplanted modified cell is decreased as compared to rejection of the cell prior to modification. The cell is prepared by a process comprising: selecting a cell for transplantation into a subject, the cell having a cell surface and antigenic determinants on the cell surface; covalently attaching a hydrophilic, biocompatible, non-immunogenicity providing compound or polymer to the cell surface directly or by means of a linking moiety, so that the hydrophilic, biocompatible, non-immunogenicity providing compound or polymer blocks the recognition of the antigenic determinants on the cell surface, to produce a non-immunogenic cell. Where the cell is part of a tissue or organ which is to be transplanted into a subject, a preferred method of carrying out the covalent attachment is to perfuse the tissue or organ with a solution of an activated polyethylene glycol or derivative thereof (i.e., the polyethylene glycol or derivative thereof is first attached to the linker molecule, forming an activated PEG, which is then perfused over the tissue or organ). During the perfusion, the activated PEG covalently attaches to the cell surface via a linking moiety.

The invention provides a method of decreasing antibody-induced aggregation of cells, the method comprising: covalently attaching to the cell surface hydrophilic, biocompatible, non-immunogenicity providing compound or polymer capable of blocking recognition of antigenic determinants on the cell surface; wherein the compounds are covalently attached to the cell surface of each of a plurality of cells, directly or by linking moieties, so as to produce non-aggregating cells, wherein antibody-induced aggregation of the non-aggregating cells is decreased as compared to antibody-induced aggregation of the cells prior to attachment of the compounds. This method is particularly applicable where the cells are red blood cells, and where the antigenic determinants on the cell surface comprise blood group antigenic determinants.

In each of the above-described methods, a linker molecule can be first reacted with the hydrophilic, biocompatible, non-immunogenicity providing compound or polymer (forming an "activated" compound) and then the linker molecule can be reacted with the cell surface. The order of these steps can be reversed, and any reference to the two steps is intended to cover the two steps in either order. Accordingly, the linker molecule can also be attached to the cell surface, then the hydrophilic, biocompatible, non-immunogenicity providing compound or polymer can be reacted with the linker molecule to bind it to the cell surface via a thus-formed linking moiety, in accordance with the claims and disclosure herein.

In the examples which follow, PEG modification of the external aspect of the red blood cell membrane effectively 'hides' major antigenic determinants such as ABO blood group substances. This is evident in the (1) lack of gross antibody-induced agglutination, (2) significantly decreased antibody-induced aggregation, and (3) diminished phagocytosis by heterologous macrophages. Treated red blood cells remain intact, exhibiting only minor spontaneous hemolysis, and demonstrate normal osmotic fragility over at least 48 hours in vitro incubation. The "normal" nature of the modified mouse red blood cell is further demonstrated by normal in vivo survival.

The PEG modification procedure is surprisingly well tolerated by the cells, yielding a product which survives normally in the circulation. The derivatized cells are antigenically disguised and not recognized by blood group antibodies or by phagocytes. Perhaps most surprisingly, treated red blood cells from one species survive much longer than do untreated red blood cells in the circulation of another species.

The invention thus provides for (1) derivatization of human red blood cells to permit transfusions into people difficult to match (because they have pre-existing antibodies to minor blood groups); (2) derivatization of human red blood cells to permit transfusions into people of unknown blood groups who may even differ in major (e.g., ABO) blood groups from the donor; (3) derivatization—by perfusion of activated mPEG solutions—of human organ grafts to prevent unexpected hyperacute rejection episodes; (4) derivatization—by perfusion of activated mPEG solutions—of organs from non-human animals to prevent hyperacute rejection and to improve the chances of ultimate successful engraftment in humans.

EXAMPLE I

Inhibition of Red Blood Cell Agglutination

Normal red blood cells (erythrocytes) were washed 3× in isotonic saline. A red blood cell suspension of hematocrit about 12% is prepared in isotonic alkaline phosphate buffer (PBS; 50 mM $K_2HPO_4$ and 105 mM NaCl, pH about 9.2). Cyanuric chloride-activated methoxypolyethylene glycol (Sigma Chemical Co.) is added and the red cells are incubated for 30 minutes at 4° C. Cell derivatization can also be done under other pH and temperature conditions with comparable results to those presented. For example, red blood cells derivatized at pH 8.0 for 60 minutes at 22° C. demonstrated virtually identical characteristics to those derivatized at pH 9.2 for 30 minutes at 4° C. The extreme range of pH and temperature conditions make this procedure broadly applicable to a wide range of cells and tissues. The proposed mechanism of covalent reaction with external proteins and other membrane components is outlined below. Typical activated mPEG concentrations used range from 0 to 8 mg per ml of red blood cell suspension. The typical activated mPEG concentration to be used on other anuclear (i.e., platelets) and various nucleated cells (e.g., vascular endothelial, hepatic, hematopoietic, neuronal, pancreatic cells, epithelial cells, etc.) can readily be determined in view of the teachings herein.

Figure 3:
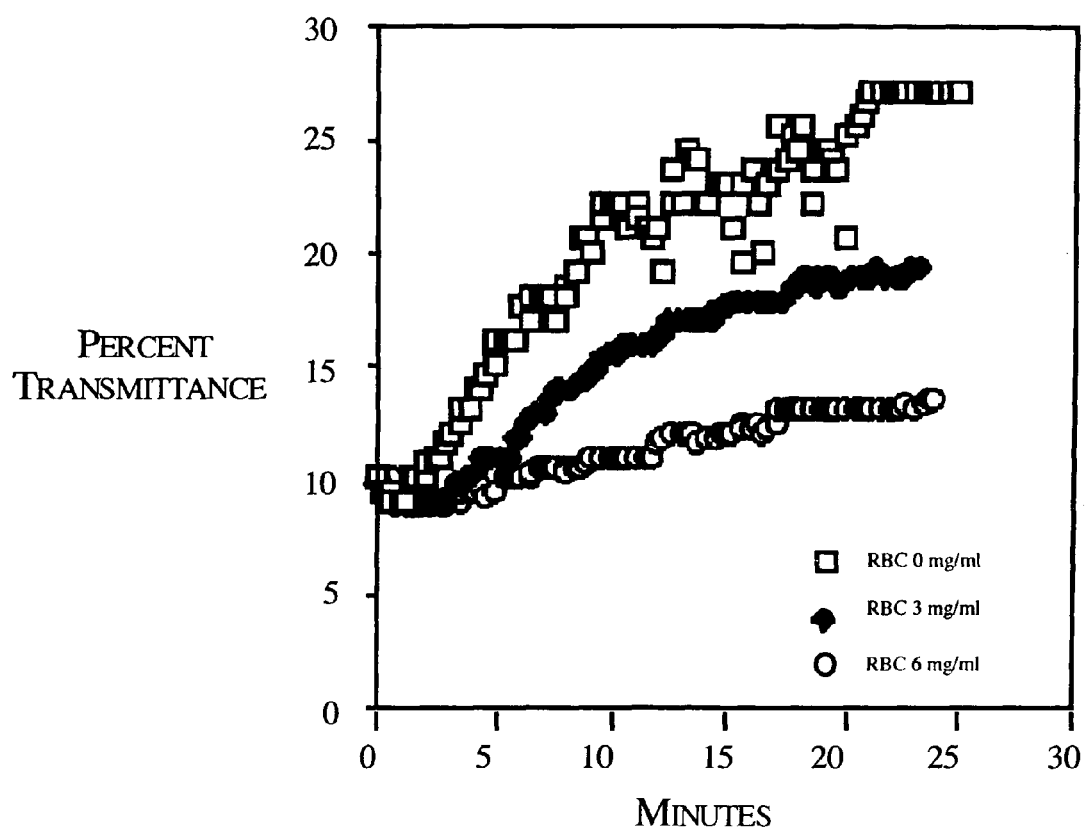
FIG. 3 is a graph showing that monomethoxypoly(ethylene glycol) (mPEG) modification of red blood cells causes a dose-dependent inhibition of anti-A antibody induced RBC aggregation defined turbidometrically.

As shown in FIG. 3, the covalent binding of mPEG to the membrane proteins of intact red blood cells prevents red blood cell agglutination. This is apparent at the gross level using agglutination induced by ABO antibodies, and at a finer level using a platelet aggregometer modified to measure red blood cell aggregation (FIG. 3). Type A red blood cells were treated with 0, 3, or 6 mg cyanuric chloride-activated mPEG (m.w. 5000) per ml of blood and incubated at 4° C. for 30 minutes. The cells were washed 3 times with isotonic saline and resuspended to a 40% hematocrit in saline.

For gross agglutination, equal volume of a RBC suspension of hematocrit 40% and a commercially available anti-A blood typing antibody (Carolina Biological Supply) were mixed and photographed. Increasing amounts of bound mPEG effectively inhibited the agglutination reaction. In the absence of derivatization, a typical blood typing response was observed. In contrast, with increasing amounts of covalently bound mPEG, a dose-dependent decrease in sera-induced agglutination of RBC was observed. Indeed, at 6 mg mPEG/ml RBC, no detectable agglutination was observed at the gross level.

FIG. 3 shows red blood cell microaggregation as measured at 37° C. in a platelet aggregometer. As shown, mPEG modification caused a dose-dependent inhibition of anti-A antibody induced red blood cell aggregation.

Further testing of matched control and mPEG-derivatized RBC selected minor RBC antigens also demonstrated a significant decrease in the antigenicity of the mPEG-modified RBC (Table 2).

TABLE 2

Detection of Selected Rh and MNS PBS Antigens on Control and Derivatized RBC

| Antigen | C | c | E | e | K | S | s |
|---|---|---|---|---|---|---|---|
| Control | 0 | $4^+$ | 0 | $3^+$ | 0 | $3^+$ | $3^+$ |
| mPEG-Treated | 0 | $1^{+w}$ | 0 | $1^{+w}$ | 0 | $1^+$ | $1^{+w}$ |

Agglutination response is measured macroscopically with a $4+^s$ rating being the strongest and $1+^w$ being the weakest agglutination response. As shown, in all cases where a minor RBC antigen was detected, mPEG-modification virtually abolished its detection (e.g., $4^+$ to $1^{+w}$). Importantly, the degree of activated mPEG derivatization used in this study was relatively low (6 mg/ml) in comparison to the levels which can be used (up to approximately 30 mg mPEG/ml RBC) while exhibiting no adverse effects on the RBC. Indeed, based on the mPEG-dose dependency noted in FIG. 3, it is very likely that higher degrees of derivatization will likely further suppress antigen detection.

EXAMPLE II

Effect on Red Blood Cell Stability

Figure 4:
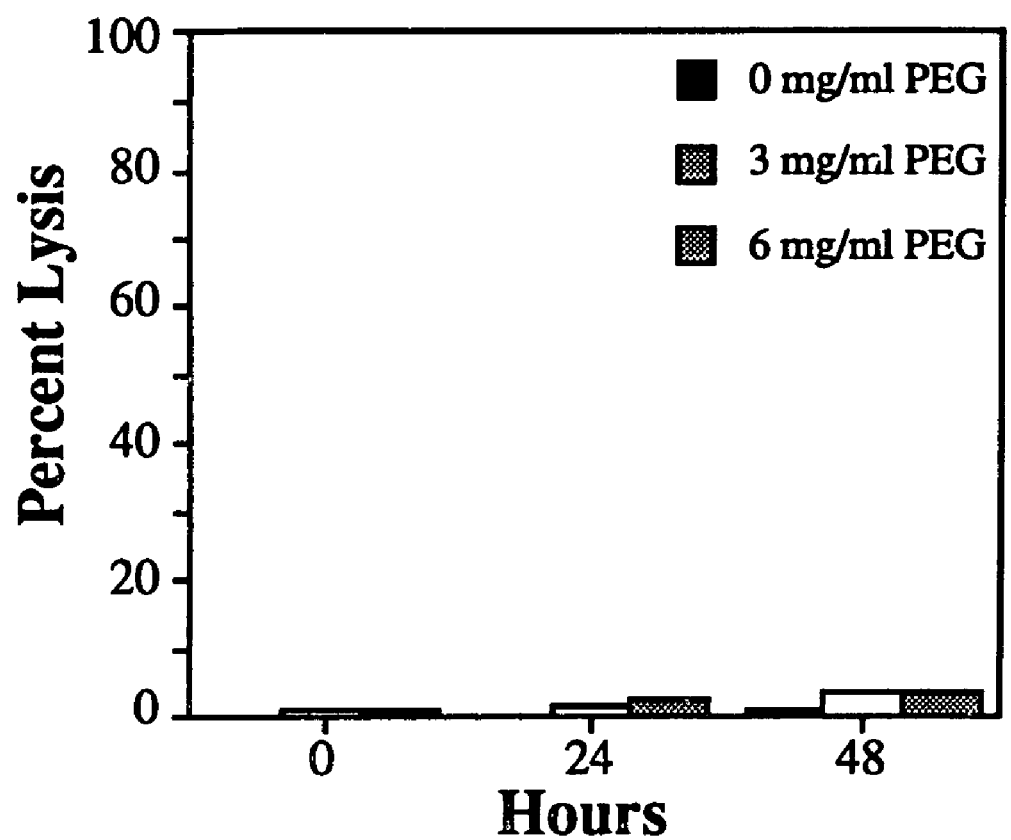
FIG. 4 is a bar graph showing that mPEG modification of red blood cells only slightly increases red blood cell lysis.
Figure 5:
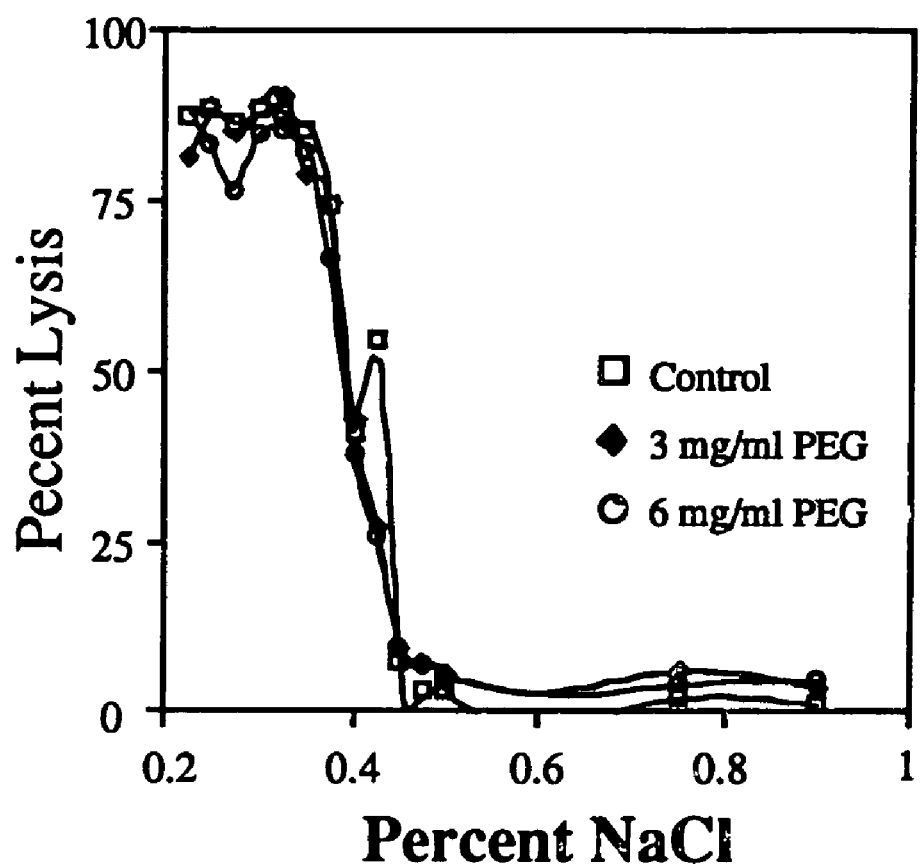
FIG. 5 is a graph showing the mPEG modification of red blood cells has no effect on red blood cell osmotic fragility.

While mPEG-modification of red blood cells slightly increases red blood cell lysis, this lysis is less than 5% of the total red blood cell mass (FIG. 4). Furthermore, mPEG-attachment was found to have no effect on red blood cell osmotic fragility (FIG. 5). Red blood cell stability was minimally modified by the covalent attachment of mPEG. As shown in FIG. 4, red blood cell lysis was slightly increased by the attachment of mPEG. However, red blood cell lysis of the RBC during mPEG modification followed by 24 hours storage at 4° C. or after incubation at 37° C. was less than 5%. As shown in FIG. 5, osmotic fragility of the mPEG-treated red blood cells was also unaffected. Shown are the osmotic fragility profiles of control and mPEG-modified (3 and 6 mg/ml) red blood cells after 48 hours incubation at 37° C. Again, while a very minor increase in spontaneous lysis was observed, no significance differences in the osmotic lysis profiles were seen. Electron micrographic analysis of control and mPEG-derivatized RBC also demonstrate no apparent structural changes.

EXAMPLE III

Figure 6:
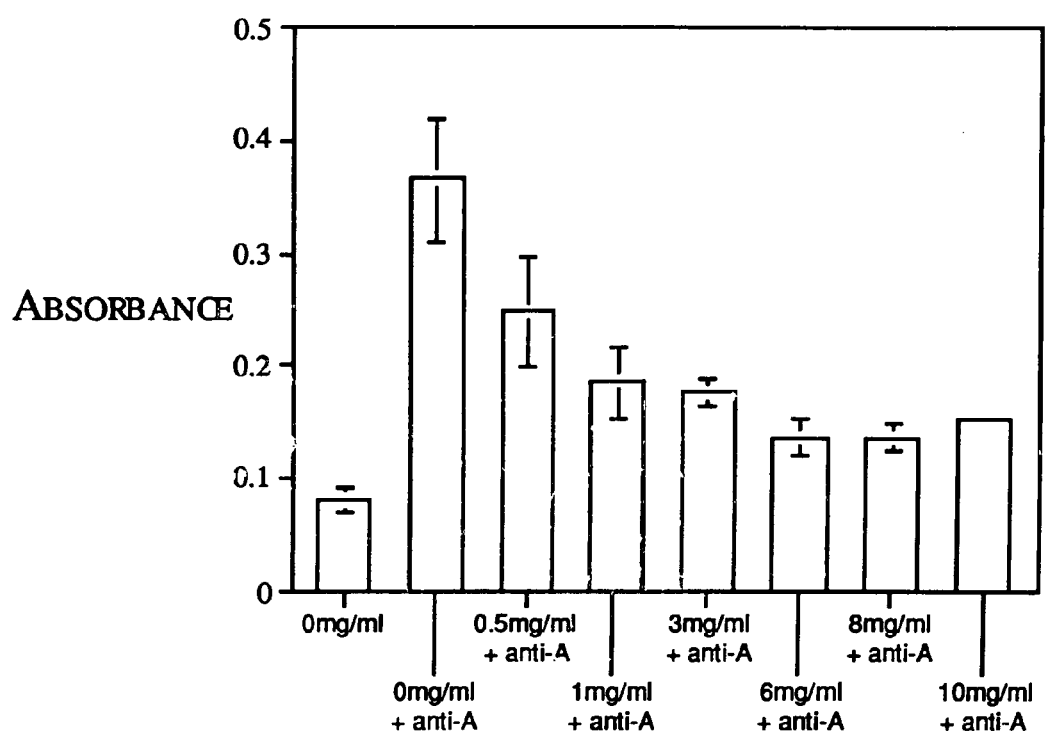
FIG. 6 is a bar graph showing that mPEG-modified type A red blood cells bind significantly less anti-A antibody.

Inhibition of Antibody Binding mPEG-modified red blood cells bind significantly less anti-A antibody (FIG. 6). As shown in FIG. 6, an ELISA assay of mPEG-treated human blood type $A^-$ red blood cells demonstrates significantly less antibody binding by mPEG-modified red blood cells. The control and mPEG red blood cells were mixed with an IgG anti-A antibody incubated for 30 minutes. The samples were extensively washed and a secondary antibody (anti-human IgG conjugated with alkaline phosphatase) was added to quantitate bound anti-Blood group A antibody.

EXAMPLE IV

Figure 7:
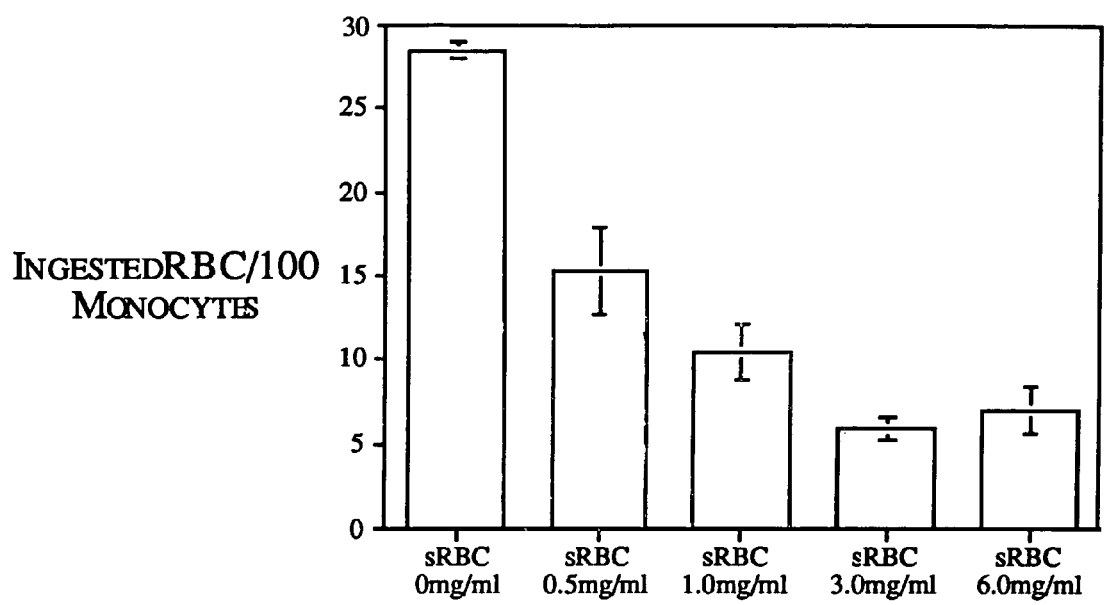
FIG. 7 is a bar graph showing that mPEG-modified sheep red blood cells are significantly less prone to phagocytosis by human peripheral blood monocytes.

Inhibition of Phagocytosis of Foreign Cells mPEG-modified sheep red blood cells are significantly less prone to phagocytosis by human peripheral blood monocytes (FIG. 7). As would be indicated by decreased antibody binding (FIG. 6), mPEG-modified sheep red blood cells are significantly less susceptible to IgG-mediated phagocytosis by human peripheral blood monocytes. mPEG-modified sheep red blood cells were incubated with human peripheral blood monocytic cells for 30 minutes. The uningested red blood cells were removed by hypotonic lysis and the number of monocytes containing sheep red blood cells, as well as the number of sheep red blood cells ingested, were determined microscopically.

Figure 8:
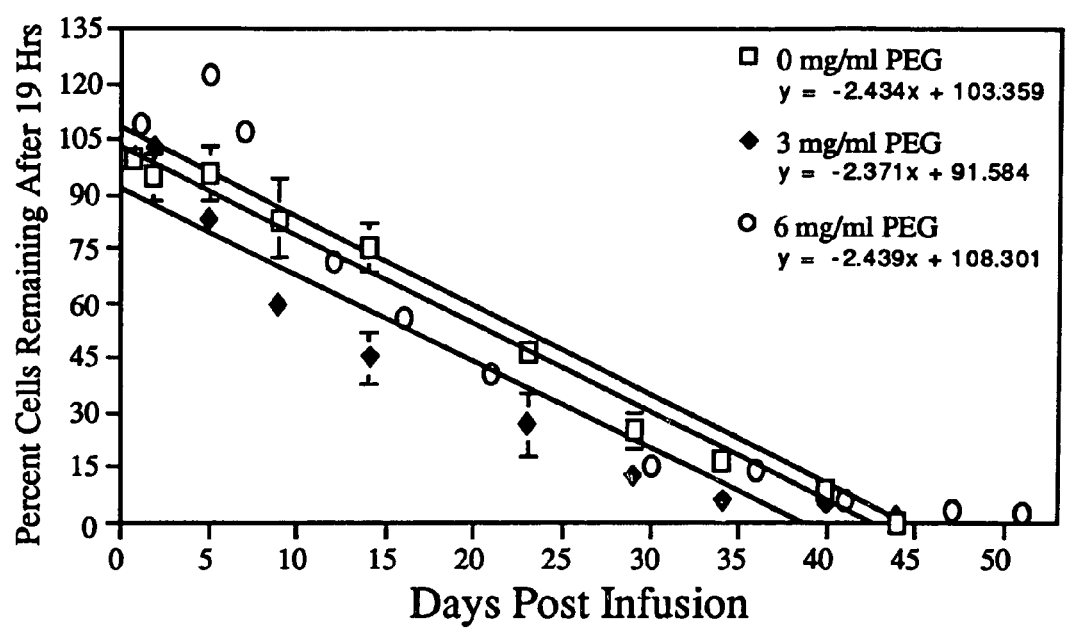
FIG. 8 is a graph showing no significant differences in the in vivo survival of control mouse red blood cells and mouse red blood cells modified with activated PEG.

EXAMPLE V mPEG-Derivatized Mouse Red Blood Cells have Normal In Vivo Survival As shown in FIG. 8, no significant differences were noted in the in vivo survival of control red blood cells and red blood cells modified with either 3 or 6 mg/ml activated mPEG. In vivo survival of control and mPEG-modified mouse red blood cells was determined using a fluorescent fatty acid label (PKH-26; Sigma Chemical Company). Blood was obtained from donor BALB/C mice, treated with 0, 3, or 6 mg/ml activated mPEG and washed thrice. The washed cells were then labeled with PKH-26 and injected i.p. into naive BALB/C mice. Blood samples were obtained by tail-cuts at the indicated time points and analyzed via FACScan.

Figure 9:
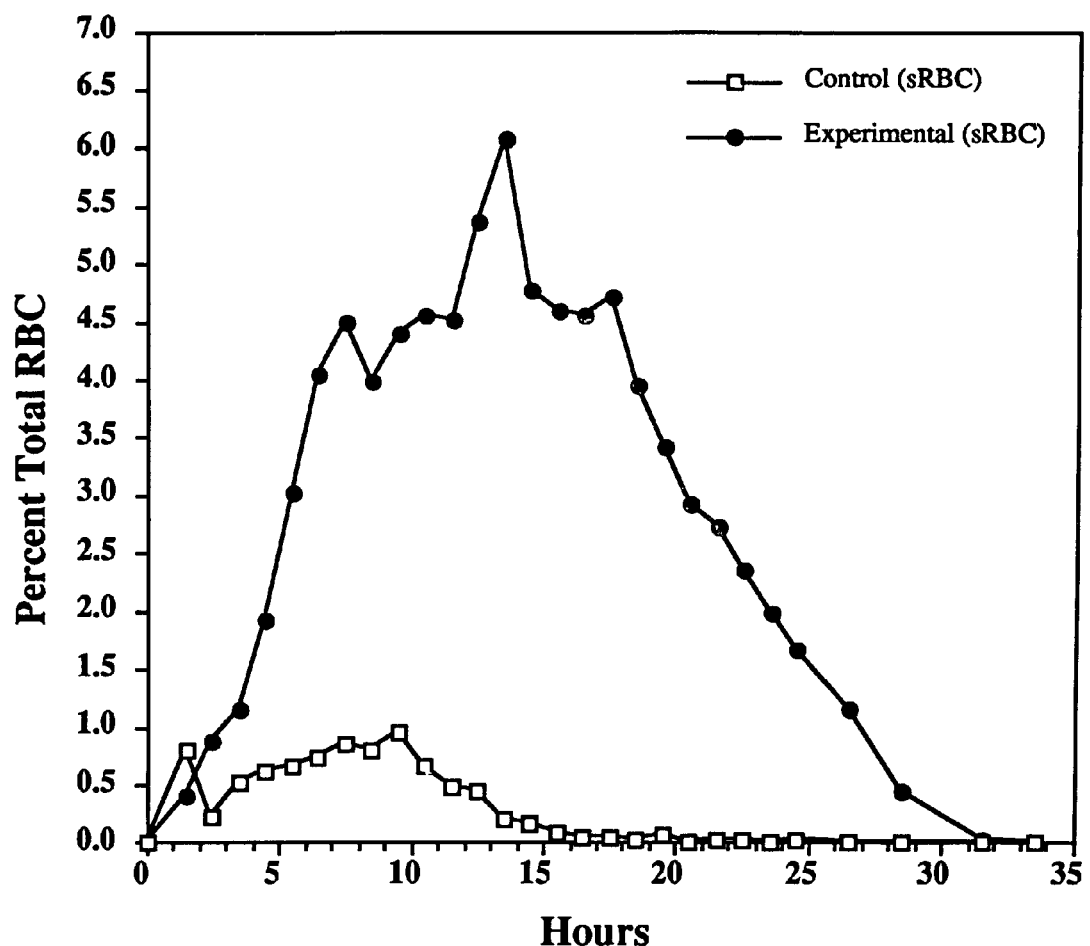
FIG. 9 is a graph demonstrating that sheep red blood cells (solid symbols) enter and survive within the circulatory system of a mouse whereas unmodified sheep red blood cells (open symbols) do not.

EXAMPLE VI mPEG-Derivatization of Sheep Red Blood Cells Results in Enhanced In Vivo Survival in Mice Comparable numbers of mPEG-modified sheep red blood cells (mPEG-sRBC) were injected i.p. into BALB/C mice. As shown in FIG. 9, mPEG-sRBC showed a greater rate of entry into the peripheral circulation and demonstrated longer in vivo survival in mice. In vivo survival of mPEG-sRBC in mice was determined using a fluorescent fatty acid label (PKH-26; Sigma Chemical Company). Blood was obtained from a donor sheep and treated with 0 or 6 mg/ml activated mPEG and washed thrice. The washed sheep red blood cells were labeled with PKH-26 and injected i.p. into naive BALB/C mice. Blood samples were obtained by tail-cuts at the indicated time points and analyzed via FACScan.

EXAMPLE VII mPEG-Modulated Lymphocytes

Figure 10:
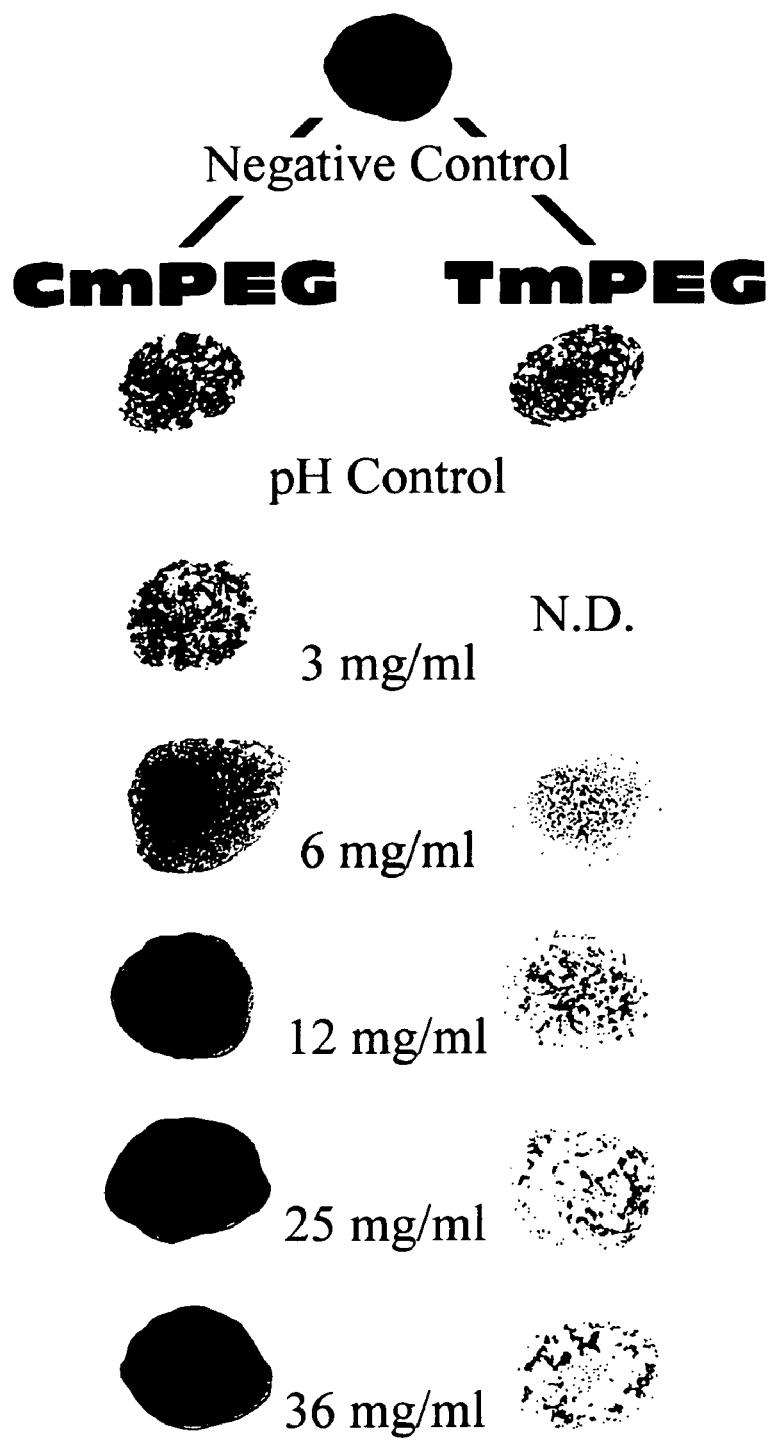
FIG. 10 shows a copy of a paper test of Gross Red Blood Cell (RBC) agglutination for tresylated PEG versus Cyanuric chloride bound PEG.
Figure 11A:
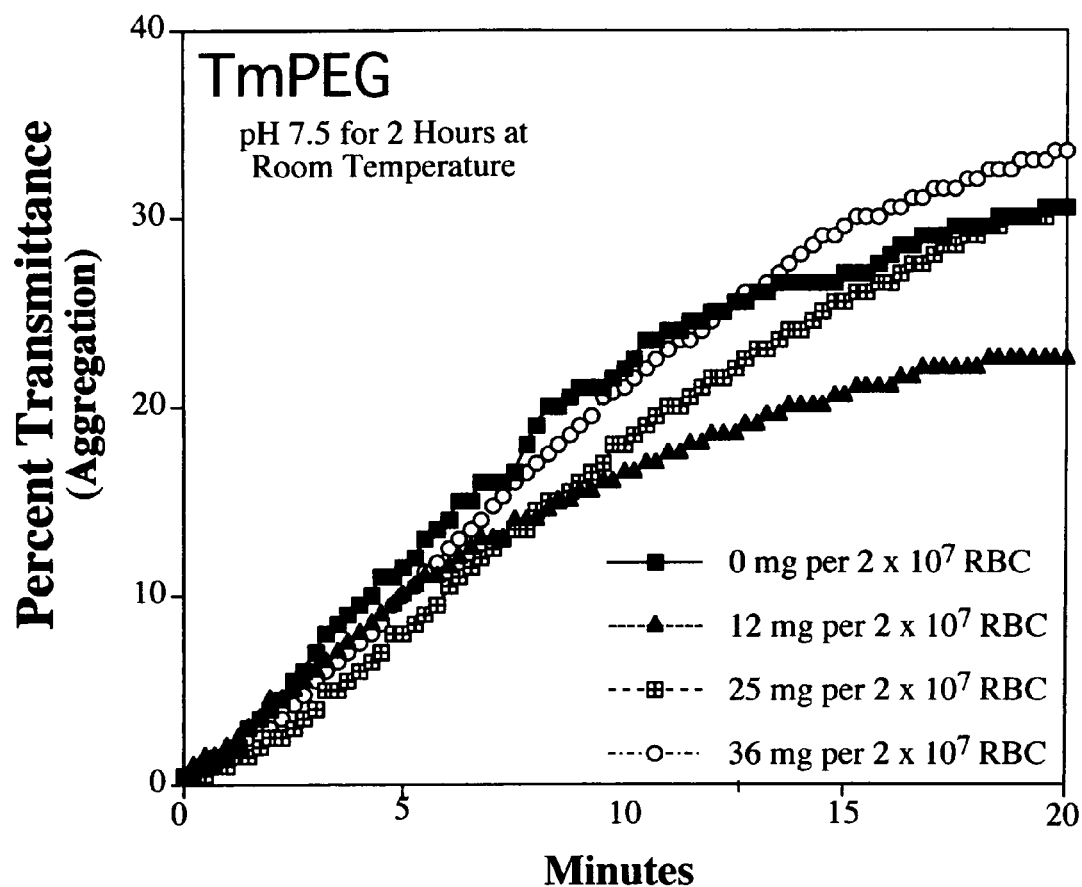
FIGS. 11a and 11b show the microaggregation curves of the tresylated activated PEG versus the cyanuric chloride activated PEG red blood cells.
Figure 11B:
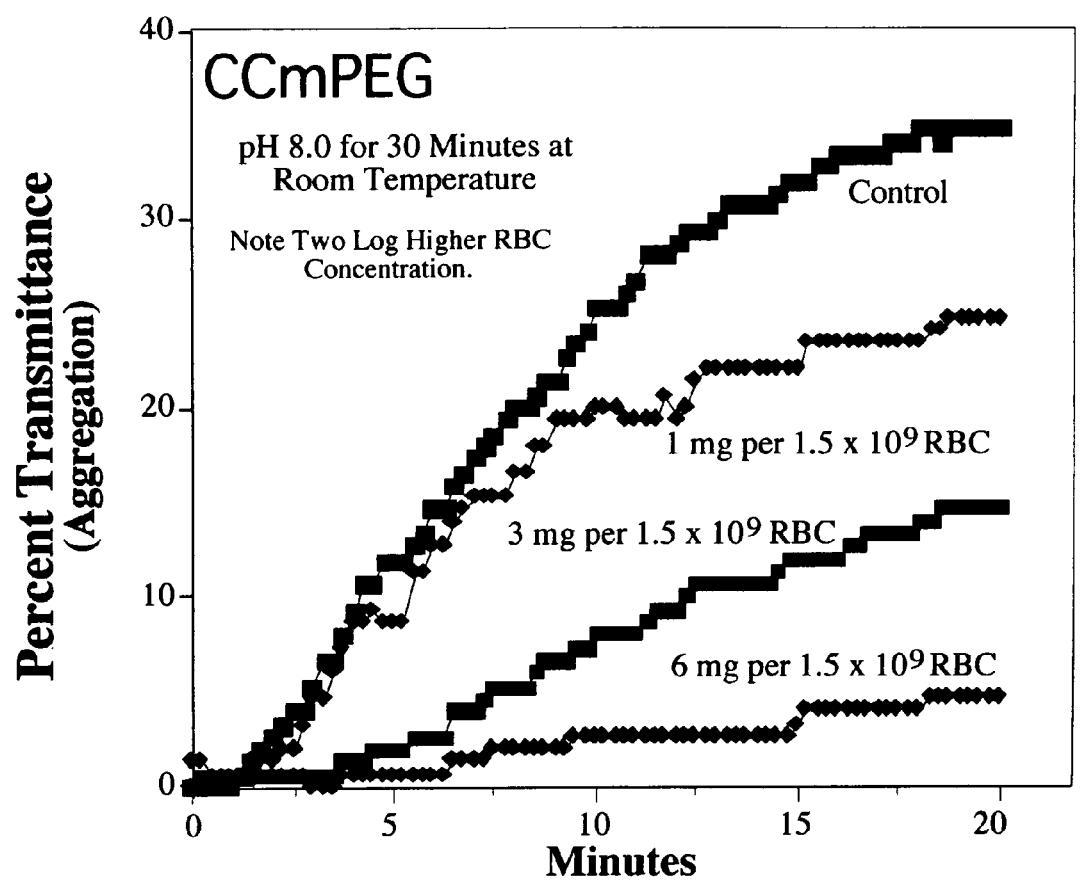

The mixed lymphocyte culture (MLC) is a very sensitive measure of histocompatibility between donor and recipient. Indeed, though time consuming, this assay is perhaps the best indicator of the probability of tissue transplant survival in the organ recipient. Primarily the MLC measures the antigenic variance between the HLA complex (the primary antigens responsible for tissue compatibility in transplants) between two individuals. As shown in FIG. 10, covalent modification with mPEG of lymphocytes from either donor results in a virtually complete inhibition of recognition of the antigenically foreign lymphocytes. Shown is the proliferation, measured by $^3$H-thymidine incorporation into DNA, of responder cells in response to a fixed concentration ($2.5 \times 10^5$ PBMC) of stimulator (i.e., cells irradiated to prevent cell replication). Panel A demonstrates PBMC Donor A's response to antigenically foreign Donor B PBMC. Panel B demonstrates Donor B's response to Donor A. In contrast, the population of responder (i.e., nonirradiated) cell expands tremendously in response to control irradiated PBMC (peripheral blood mononuclear cells).

These results are further confirmed by photomicrographs of the mixed lymphocyte cultures. Extensive proliferation, cell spreading, and expansive foci of responder cells are seen in response to control stimulator cells. In contrast, the same population of responder cells fails to recognize mPEG-treated stimulator cells, remain morphologically unactivated and fail to proliferate.

EXAMPLE VIII

Modification of Platelets

Figure 12:
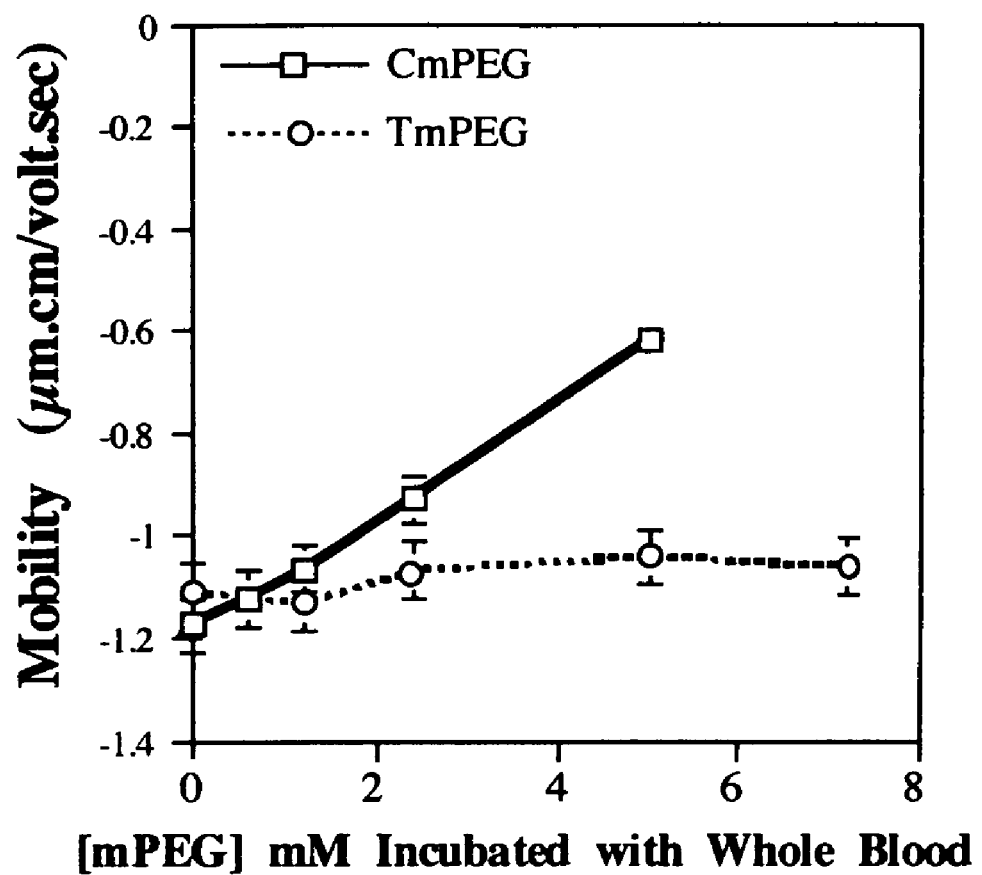
FIG. 12 shows the mobility curves for the tresylated activated PEG versus the cyanuric chloride activated PEG.

Other blood cells are also amenable to mPEG modification. Platelets were modified at pH 8.0 for 60 minutes at room temperature by the procedure of Example 1. The dotted line represents platelet rich plasma (PRP) in the absence of ADP (i.e., control unactivated platelets). As demonstrated in FIG. 12, mPEG derivatized platelets do not aggregate in response to activation by ADP (5 µM). While control platelets are fully aggregated within approximately 2 minutes, mPEG-modified platelets remain unaggregated even after 7 minutes of exposure to ADP. The loss of aggregation is mediated by disruption of cell:cell interaction (i.e., preventing platelet interaction and microaggregate formation). Indeed, alteration in cell:cell interaction is a primary event due to the covalent modification of cell surfaces with non-immunogenic materials.

EXAMPLE IX

Modification of Epithelial Cells

To determine if non-hematological cells could be antigenically modified by mPEG-derivatization, a breast carcinoma epithelial cell line (MCF7) was examined. A mouse monoclonal antibody directed towards epithelial specific antigen (ESA; a 40 kD glycoprotein) was chosen. Mouse anti-human ESA binding was quantitated using a BD-FACScan. FITC-conjugated goat anti-mouse antibody was used to detect bound ESA. Epithelial cell concentration was $5 \times 10^5$ cells/ml with a 1:6000 titre of anti-ESA antibody. Epithelial cells were derivatized using a modification of the RBC-derivatization protocol. Specifically, confluent monolayers of MCF7 cells were scraped from tissue culture flasks and suspended in RPMI media. The cell suspensions were incubated with increasing concentrations of activated mPEG at pH 8.0 and incubated at room temperature for 60 minutes. The cells were then washed 3× with culture media prior to the antibody binding assay.

A mPEG-dose dependent decrease in ESA-specific antibody binding was observed. At the highest mPEG dosage used (8 mg/ml cells) a >70% decrease in anti-ESA binding was observed.

The covalent modification of the external cell membrane with non-immunogenic materials (e.g., mPEG) effectively "hides" both major and minor antigenic determinants on a large variety of nucleated and anucleated cells. The covalent attachment of non-immunogenic materials to intact cells (e.g., RBC, endothelial cells, epithelial cells, pancreatic β cells, etc.) can be used for: (1) Derivatization of human red cells to permit transfusions into people difficult to match (because they have pre-existing antibodies to minor blood groups); (2) Derivatization of human red cells to permit transfusions into people of unknown blood groups who may even differ in major (e.g., ABO) blood groups from the donor; (3) Derivatization, by perfusion of mPEG solutions, of human organ grafts to prevent unexpected hyperacute rejection episodes; (4) Derivatization—by perfusion of mPEG solutions—of organs from non-human animals to prevent hyperacute rejection and to improve the chances of ultimate successful engraftment.

When prepared with tresylated mPEG as stated in the patent/manuscript in question, the PEG-modified cells are not protected from antibody-induced agglutination. Furthermore, in vivo RBC survival is decreased in a mouse model and TmPEG modification readily kills nucleated cells (peripheral blood mononuclear cells (PBMC)).

Antibody-Mediated Aggregation of Red Blood Cells. Blood type $A^-$ erythrocytes were covalently modified with the indicated concentrations of tresylated poly(ethylene glycol) [TmPEG] or cyanuric chloride activated poly(ethylene glycol) [CCmPEG]. Red cell microaggregation was measured at 37° C. in a platelet aggregometer using a commercially available anti-A blood typing sera (Carolina Biological Supply). As shown, TmPEG modification (as per the method of Francis*) does not result in reduced antibody-mediated agglutination. In contrast, surface modification using the method of Scott et al. results in a dose-dependent inhibition of Anti-A antibody induced RBC aggregation at concentrations (expressed on a per cell basis) several fold lower.

These results demonstrate that using the method Francis, no decrease in RBC agglutination could be observed, nor does it imply that there is any immunological protection conferred by the method of Francis against antibody recognition of the red cell surface.

FIG. 1. Antibody-Mediated Aggregation of Red Blood Cells. Type $A^-$ RBC were incubated with a commercial anti-A antibody. Gross RBC agglutination (left; mg per $5\times10^9$ RBC-[whole blood]) was observed as were the microaggregation curves of the tresylated (TmPEG; upper right) and cyanuric chloride (CCmPEG; lower right) activated methoxy poly(ethylene glycol). *Note in right-hand figures, the method of Francis et al. used approximately 36 mg TmPEG per $2\times10^7$ RBC vs. our CCmPEG studies using $10^9$ RBC.

Particle Electrophoresis Measurements on PEGylated Human RBCs

Particle electrophoresis of control and pegylated (CmPEG and TmPEG) was also done in order to assess whether these compounds differentially altered the electrophoretic mobility of the intact cells. Particle electrophoresis directly measures the electrokinetic behavior of particles (e.g., red blood cells) and is extremely sensitive such that it can detect even very small changes in cell surface charge. In addition, the electrophoretic mobility of particles is affected by the addition of neutral polymeric headgroups (such as PEG) which alters the hydrodynamic properties of the surface region. Consequently, modification of RBC with PEG should be observed as a reduction in the mobility of the RBCs due to an increase in drag force associated with the presence of PEG extending from the RBC surface. By using this assay, it is possible to semi-quantitatively measure the efficacy of derivatization of the cell surface and to approximate the degree of immunocamouflage by the different linker groups used to covalently attach mPEG.

PEGylation Protocol. Blood was collected from human volunteers in lithium heparin vacutainer tubes. PEG solutions were made up in phosphate-buffered saline (50 mM dibasic potassium phosphate, 105 mM NaCl) with the CmPEG at pH 8.0 and the TmPEG at pH 7.4. Whole blood (0.15 ml) was then reacted with 0.15 ml of different concentrations of PEG solutions. All reactions were done at room temperature. The CmPEG samples were incubated for 30 minutes while the TmPEG RBC were derivatized for 1 hour. The modified RBCs were then washed twice with PBS followed by two more washings with isotonic saline.

Electrophoresis Measurements and General Principle. Mobility measurements of the control and pegylated RBC were made on a Rank Mark I electrophoresis apparatus equipped with a horizontal microscope having a water immersion lens. The migration of individual RBCs in an applied electric field was timed manually. Ten different RBCs were chosen randomly and were timed to determine their velocity in the field. The electrophoretic mobility was determined as: mobility=velocity of the particle (μm/sec)/electric field strength (E) in volt/cm; where E=(voltage/distance between the electrodes).

Results. A significant mobility shift for RBCs modified with CmPEG was readily observed in all samples derivatized with ≧1.2 mM CmPEG. As noted in FIG. 2, the mobility of the CmPEG RBC shifted toward zero due to the increased drag force arising from the presence of PEG extending out from the RBC surface. This indicates successful, dose-dependent, derivitization of RBC. In contrast, TmPEG at comparable dosages had no significant effect on RBC mobility indicating that the TmPEG procedure as taught by Francis fails to significantly modify the RBC surface. Indeed, as demonstrated on the previous page, the method of Francis yields cells that exhibit no immunological modification.

FIG. 2. Particle electrophoresis of CmPEG and TmPEG. As shown, CmPEG readily modifies the RBC surface and confers immunocamouflage. In contrast, the TmPEG method as taught by Francis fails to significantly modify RBC and does not yield any protection from immune recognition (FIG. 1). Show the mean±S.D. of 10 independent experiments.

Nucleated Cells

Furthermore, application of the Francis method to nucleated cells results in significant cellular toxicity. This is readily seen with human or murine peripheral blood mononuclear cells (PBMC). When cell viability is determined via flow cytometry using a vital dye (propidium iodide), the method of Francis yields dead or dying cells (Table A). In contrast, utilizing our methodology, we maintain the viability of the cells (Table B). In additional data, we can also readily demonstrate that the method of Francis et al. does not camouflage the cell surface of the PBMC while our methodology does so quite effectively.

In sum, based on the results one would have obtained using the exact methodology of Francis et al., anucleate and nucleated cells are not immunocamouflaged nor, especially in the case of nucleated cells, are they viable.

TABLE A

Viability of PBMC Treated with TmPEG

| Concentration | Actual Viability | | % Relative to Control | |
|---|---|---|---|---|
| | 0 Hours | 72 Hours | 0 Hours | 72 Hours |
| Control | 95.0% | 48.5% | 100.0% | 100.0% |
| 0 mg per $5.12 \times 10^6$ PBMC | 95.2% | 35.7% | 100.2% | 73.6% |
| 1 mg per $5.12 \times 10^6$ PBMC | nd | 6.3% | nd | 13.0% |
| 3 mg per $5.12 \times 10^6$ PBMC | nd | 0.0% | nd | 0.0% |
| 6 mg per $5.12 \times 10^6$ PBMC | 91.1% | 0.0% | 95.9% | 0.0% |
| 12 mg per $5.12 \times 10^6$ PBMC | 89.0% | 0.0% | 93.7% | 0.0% |
| 25 mg per $5.12 \times 10^6$ PBMC | 51.8% | 0.0% | 54.5% | 0.0% | nd—not determined

TABLE B

Viability of PBMC Treated with CCmPEG

| Concentration | Actual Viability | | % Relative to Control | |
|---|---|---|---|---|
| | 0 Hours | 96 Hours | 0 Hours | 96 Hours |
| Control | 95.0% | 81.5% | 100.0% | 100.0% |
| 0 mg per $5.12 \times 10^6$ PBMC | 96.5% | 80.2% | 101.6% | 98.4% |
| 1 mg per $5.12 \times 10^6$ PBMC | nd | nd | nd | nd |
| 3 mg per $5.12 \times 10^6$ PBMC | nd | nd | nd | nd |
| 6 mg per $5.12 \times 10^6$ PBMC | 94.7% | 74.6% | 99.7% | 91.5% |
| 12 mg per $5.12 \times 10^6$ PBMC | 91.2% | 75.0% | 96.0% | 92.0% |
| 20 mg per $5.12 \times 10^6$ PBMC | 83.1% | 68.1% | 87.5% | 83.6% | nd - not determined
CCmPEG = Cyanuric Chloride Activated Methoxypoly(ethylene Glycol)
$CH_3(-O-CH_2-CH_2)_n-O$

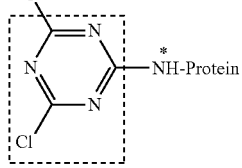

Leaving Group: None
TmPEG=Tresylchloride Activated (Tresylated) Methoxypoly(ethylene Glycol)

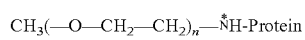

Leaving Group: $OSO_2CH_2CF_3$

Our data suggests that the $OSO_2CH_2CF_3$ moiety may exert a potent toxic effect on nucleated cells.

All cited patents and publications are incorporated by reference herein, as though fully set forth. Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Abuchowski, A. et al. (1977a) Alteration of immunological properties of bovine serum albumin by covalent attachment of polyethylene glycol. *J. Biol. Chem.*, 252:3358-3581.

Abuchowski, A. et al. (1977b) Effect of covalent attachment of polyethylene glycol on immunogenicity and circulating life of bovine liver catalase. *J. Biol. Chem.*, 252:33823586.

Harris, J. M. et al. (1984) Synthesis and characterization of Poly(ethylene Glycol) Derivatives. *J. Poly. Sci.*, 22:341:352.

Harris, J. M. (1985) Laboratory Synthesis of Polyethylene Glycol Derivatives. *Journal of Macromolecular Sciences Reviews in Macromolecular chemistry and Physics*, C25: 325-373.

Jackson, C-J. et al. (1987) Synthesis, isolation, and characterization of conjugates of ovalbumin with monomethoxy-polyethylene glycol using cyanuric chloride as the coupling agent. *Anal. Biochem.*, 165:114-127.

Klibanov, A. L. et al. (1991) Activity of amphipathic poly (ethylene glycol) 5000 to prolong the circulation time of liposomes depends on the liposome size and is unfavorable for immunoliposome binding to target. *Biochim. Biophys. Acta*, 1062:2782-1794.

Lacy, P. E. et al. (1991) Maintenance of Normoglycemia in Diabetic Mice by Subcutaneous Xenografts of Encapsulated Islets. *Science*, 254:1782-1794.

Lasic, D. (1992) Liposomes. *American Scientist*, 80:20-31.

Lim, F., and Sun, A. (1980) Microencapsulated Islets as bio-artificial endocrine Pancreas. *Science*, 210:908-910.

Maruyama, K. et al. (1992) Prolonged circulation time in vivo of large unilamellar liposomes composed of distearoyl phosphatidylcholine and cholesterol containing amphipathic poly(ethylene glycol). *Biochim. Biophys. Acta*, 1128: 44-49.

Merrill, E. W. Poly(Ethylene Oxide) and blood contact: A chronicle of one laboratory. In: *Poly(Ethylene Glycol) Chemistry: Biotechnical and Biomedical Application* (Harris, J. M., Editor) 1992, Plenum Press, N.Y., pp. 199-220.

Mitz, M. A. and Summaria L. J. (1961) Synthesis of biologically active cellulose derivatives of enzymes. *Nature*, 189: 576-577.

Park, K. D. et al. PEO-Modified Surfaces—In vitro, Ex vivo and In vivo blood compatibility. In: *Poly(Ethylene Glycol) Chemistry: Biotechnical and Biomedical Application* (Harris, J. M., editor) 1992, Plenum Press, N.Y., pp. 283-302.

Sawhney, A. S. et al. (1994) Modification of Islet of Langerhans surfaces with immunoprotective poly(ethylene glycol) coatings via interfacial photopolymerization. *Biotech. Bioeng.*, 44:383-386.

Senior, J. et al. (1991) Influence of surface hydrophilicity of liposomes on their interaction with plasma protein and clearance from the circulation: studies with poly(ethylene glycol)-coated vesicles. *Biochim. Biophys. Acta*, 1062:77-82.

Vichinsky, E. P. et al. (1990) Alloimmunization in sickle cell anemia and transfusion of racially unmatched blood. *New Eng. J. Med.*, 322:1617-1621.

von Specht, B.-U. et al. (1973) *Hoppe-Seyler's Z. Physiol. Chem.*, 354:1659-1660.

Zalipsky, S, and Lee, C. Use of functionalized Poly(Ethylene Glycol)s for modification of polypeptides. In: *Poly(Ethylene Glycol) Chemistry: Biotechnical and Biomedical Application* (Harris, J. M., editor) 1992, Plenum Press, N.Y., pp. 347-370.

Poly(Ethylene Glycol) Chemistry: Biotechnical and Biomedical Application. Harris, J. M., editor (1992), Plenum Press, NY.

What is claimed is:

1. A non-aggregating, non-immunogenic nuclear cellular composition in which at least 25% by number of nuclear cells in said composition remain viable for 96 hours consisting of:
   a) a mammalian nuclear cell having a cell surface and antigenic determinants on said surface;
   b) a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer.

2. The cellular composition of claim 1 wherein said cell is a lymphocyte and the covalently bonded hydrophilic, biocompatible, non-immunogenicity providing compound or polymer is covalently bonded to the nuclear cell through a unit derived from reaction of a cyanuric chloride linking group on the covalently bonded hydrophilic, biocompatible, non-immunogenicity providing compound or polymer to the cell surface.

3. The cellular composition of claim 1 wherein linking moieties covalently attach the hydrophilic, biocompatible, non-immunogenicity providing compound or polymer to said surface, said linking moieties are covalently attached to said antigenic determinants on said cell surface and said nucleated cell is a vascular endothelial cell.

4. The cellular composition of claim 1 wherein linking moieties covalently attach the hydrophilic, biocompatible, non-immunogenicity providing compound or polymer to said surface, said linking moieties are covalently attached to said antigenic determinants on said cell surface and said nucleated cell is a hepatic cell.

5. The cellular composition of claim 1 wherein linking moieties covalently attach the hydrophilic, biocompatible, non-immunogenicity providing compound or polymer to said surface, said linking moieties are covalently attached to said antigenic determinants on said cell surface and said nucleated cell is a neuronal cell.

6. The cellular composition of claim 5 wherein said cell is part of a tissue or organ and the covalently bonded hydrophilic, biocompatible, non-immunogenicity providing compound or polymer is covalently bonded to the nuclear cell through a unit derived from reaction of a cyanuric chloride linking group on the covalently bonded hydrophilic, biocompatible, non-immunogenicity providing compound or polymer to the cell surface.

7. The cellular composition of claim 1 wherein linking moieties covalently attach the hydrophilic, biocompatible, non-immunogenicity providing compound or polymer to said surface, said linking moieties are covalently attached to said antigenic determinants on said cell surface and said nucleated cell is a pancreatic cell.

8. The cellular composition of claim 1 wherein linking moieties covalently attach the hydrophilic, biocompatible, non-immunogenicity providing compound or polymer to said surface, said linking moieties are covalently attached to said antigenic determinants on said cell surface and said nucleated cell is an epithelial cell.

9. A non-aggregating, non-immunogenic anuclear cellular composition consisting of:
   a) a mammalian anuclear cell having a cell surface and antigenic determinants on said surface;
   a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer wherein linking moieties are covalently bonded to said antigenic determinants on said cell surface.

10. A non-aggregating, non-immunogenic anuclear cellular composition consisting of:
    a) a mammalian anuclear cell having a cell surface and antigenic determinants on said surface;
    a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer wherein said cell is an anuclear cell and the covalently bonded hydrophilic, biocompatible, non-immunogenicity providing compound or polymer is covalently bonded to the nuclear cell through a unit derived from reaction of a cyanuric chloride linking group on the covalently bonded hydrophilic, biocompatible, non-immunogenicity providing compound or polymer to the cell surface.

11. A non-aggregating, non-immunogenic anuclear cellular composition consisting of:
    b) a mammalian anuclear cell having a cell surface and antigenic determinants on said surface;
    a sufficient amount of hydrophilic, biocompatible, non-immunogenicity providing compound or polymer covalently attached to said surface so that recognition of said antigenic determinants on said surface is blocked by said covalently bonded hydrophilic, biocompatible, non-immunogenicity providing compound or polymer wherein said cell is a platelet and the covalently bonded hydrophilic, biocompatible, non-immunogenicity providing compound or polymer is covalently bonded to the nuclear cell through a unit derived from reaction of a cyanuric chloride linking group on the covalently bonded hydrophilic, biocompatible, non-immunogenicity providing compound or polymer to the cell surface.

12. A method of producing a non-immunogenic mammalian cell, said method comprising:
    covalently attaching an amount of hydrophilic, biocompatible, non-immunogenicity providing compound or polymer to the cell surface, directly or by means of a linking moiety, so that said hydrophilic, biocompatible, nonimmunogenicity providing compound or polymer blocks recognition of antigenic determinants on the cell surface and yields a non-immunogenic cell wherein linking moieties covalently attach the hydrophilic, biocompatible, non-immunogenicity providing compound or polymer to said surface, said linking moiety is covalently bonded to said antigenic determinants on said cell surface.

* * * * *